(12) United States Patent
Potter et al.

(10) Patent No.: US 8,501,792 B2
(45) Date of Patent: Aug. 6, 2013

(54) TREATING CANCER WITH DESTHIAZOLYL RITONAVIR

(76) Inventors: David A. Potter, St. Louis Park, MN (US); Monica Milani, Frejus (FR); Anjaiah Srirangam, Lexington, MA (US); Ranjana Mitra, Las Vegas, NV (US); Rory P. Remmel, Minneapolis, MN (US)

( * ) Notice: Subject to any disclaimer, the term of this patent is extended or adjusted under 35 U.S.C. 154(b) by 0 days.

(21) Appl. No.: 12/867,845

(22) PCT Filed: Feb. 17, 2009
(Under 37 CFR 1.47)

(86) PCT No.: PCT/US2009/034315
§ 371 (c)(1),
(2), (4) Date: Mar. 22, 2012

(87) PCT Pub. No.: WO2009/105430
PCT Pub. Date: Aug. 27, 2009

(65) Prior Publication Data
US 2012/0329841 A1    Dec. 27, 2012

Related U.S. Application Data

(60) Provisional application No. 61/029,773, filed on Feb. 19, 2008.

(51) Int. Cl.
*A01N 43/78*    (2006.01)
*A61K 31/425*    (2006.01)
*C07D 277/30*    (2006.01)

(52) U.S. Cl.
USPC .......................................... 514/365; 548/204

(58) Field of Classification Search
None
See application file for complete search history.

(56) References Cited

U.S. PATENT DOCUMENTS

| | | | |
|---|---|---|---|
| 5,616,720 | A | 4/1997 | Kempf et al. |
| 6,407,252 | B1 | 6/2002 | Bellani et al. |
| 2007/0009593 | A1 | 1/2007 | Potter |

FOREIGN PATENT DOCUMENTS

| | | |
|---|---|---|
| WO | WO 01/21603 | 3/2001 |
| WO | WO 2004/006847 | 1/2004 |
| WO | WO 2004/010937 | 2/2004 |
| WO | WO 2006/021456 | 3/2006 |
| WO | WO 2007/140299 | 12/2007 |

OTHER PUBLICATIONS

International Search Report and Written Opinion in International Application No. PCT/US2009/034315, dated Oct. 8, 2009, 16 pages.
International Preliminary Report on Patentability in International Application No. PCT/US2009/034315, dated Sep. 2, 2010, 8 pages.
Ansel, "Peroral Solids, Capsules, Tablets, and Controlled-Release Forms," *Introduction to Pharmaceutical Dosage Forms*, Fourth Edition, 1985, 126.
Beck et al., "Hsp90 cleavage by an oxidative stress leads to its client proteins degradation and cancer cell death," *Biochemical Pharmacology*, 2008.
Chou et al., "Quantitative analysis of dose-effect relationships: the combined effects of multiple drugs or enzyme inhibitors," *Advance Enz Regul.*, 1985, 22:27-55.
Citron et al., "Randomized Trial of Dose-Dense Versus Conventionally Scheduled and Sequential Versus concurrent Combination Chemotherapy as Postoperative Adjuvant Treatment of Node-Positive Primary Breast Cance: First Report of Intergroup Trial C9741/Cancer and Leukemia Group B Trial 9741," *J. Clin. Oncol.*, 2003, 21(8):1431-1439.
Denissen et al., "Metabolism and disposition of the HIV-1 protease inhibitor ritonavir (ABT-538) in rats, dogs, and humans," *Drug Metabolism and Disposition*, 1997, 25(4):489-501.
Gupta et al., "HIV Protease Inhibitors Block Akt Signaling and Radiosensitize Tumor Cells Both in viro and in vivo," *Cancer Res.*, 2005, 65(18):8256-8265.
Jones et al., Phase III Trial Comparing Doxorubicin Plus Cyclophosphamide with Docetaxel Plus Cyclophosphamide As Adjuvant Therapy for Operable Breast Cancer, *J. Clin. Oncol.*, 2006, 24(34):5381-5387.
Kobayashi, "A phase I study of CYP3A4 modulation of oral (po) etoposide with ketoconazole (KCZ) in patients (pts) with advanced cancer (ca)," *Proceedings of the Annual Meeting of the American Society of Clinical Oncology*, 1996, 15:A1489.
Labrie et al., "In vitro activity of novel dual action MDR anthranilamide modulators with inhibitory activity on CYP-450 (Part 2)," *Bioorganic & Medicinal Chemistry*, 2007, 15(11):3854-3868.
Labrie et al., "In vitro activity of novel dual action MDR anthranilamide modulators with inhibitory activity at CYP-450," *Bioorganic & Medicinal Chemistry*, 2006, 14(23):7972-7987.
Ohno et al., "Rapid colorimetric assay for the quantification of leukemia inhibitory factor (LIF) and interleukin-6 (IL-6)," *J Immunol Methods*, 1991, 145(1-2):199-203.
Pal et al., "MDR- and CYP3A4-mediated drug-herbal interactions," *Life Sciences*, 2006, 78(18):2131-2145.
Romond et al., "Trastuzumab plus Adjuvant Chemotherapy for Operable HER2-Positive Breast Cancer," *N. Engl. J. Med.*, 2005, 353(16):1673-1684.
Srirangam et al., Effects of HIV Protease Inhibitor Ritonavir on Akt-Regulated Cell Proliferation in Breast Cancer*Clin Cancer Res.*, 2006, 12(6):1883-96.
U.S. Dept. of Health and Human Services, National Center for Health Statistics, Health United States 1996-97 and Injury Chartbook 117 (1997).
van Erp et al., "Influence of CYP3A4 inhibition on the steady-state pharmacokinetics of imatinib," *Clinical Cancer Research*, 2007, 13(24):7394-7400.

*Primary Examiner* — James D Anderson
*Assistant Examiner* — William Lee
(74) *Attorney, Agent, or Firm* — Fish & Richardson P.C.

(57) ABSTRACT

Treatment of cancer includes administering a compound of formula I, for example des-ritonavir, to a subject. In particular, treatment of breast cancer is described.

16 Claims, 19 Drawing Sheets

TREATING CANCER WITH DESTHIAZOLYL RITONAVIR

CROSS-REFERENCE TO RELATED APPLICATIONS

This application is a National Stage application under 35 U.S.C. §371 and claims benefit under 35 U.S.C. §119(a) of International Application No. PCT/US2009/034315, having an International Filing Date of Feb. 17, 2009, which claims the benefit of U.S. provisional application Ser. No. 61/029,773, filed Feb. 19, 2008, which are hereby incorporated by reference in their entirety.

STATEMENT AS TO FEDERALLY SPONSORED RESEARCH

Certain aspects of the disclosure provided herein were supported by Grant No. R01-CA113570, granted by the National Institutes of Health. The Government has certain rights in the invention.

TECHNICAL FIELD

This disclosure relates to the treatment of cancers, for example, breast cancer, by methods that include administration of a compound of formula I, for example, desthiazolyl ritonavir. In particular, methods of treating ER+, triple negative and her2− breast cancers and lung cancer are described.

BACKGROUND

Cancer is now the second leading cause of death in the United States. In 1995, cancer accounted for 23.3% of all deaths in the United States. See, e.g., U.S. Dept. of Health and Human Services, National Center for Health Statistics, Health United States 1996-97 and Injury Chartbook 117 (1997).

Cancer is now primarily treated with one or a combination of three types of therapies: surgery; radiation; and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication, cell metabolism, or cell invasion, motility and metastasis. It is used most often in the treatment of breast, lung, and testicular cancer as well as hematologic malignancies such as leukemia and myeloma. One of the main causes of failure in this treatment of cancer is the development of drug resistance by the cancer cells, a serious problem that may lead to recurrence of disease or even death.

In one example, new treatments for breast cancer are being developed based on the understanding that the progression of breast cancer requires resistance to cell death; however, the mechanisms by which breast cancer cells acquire this attribute is not well understood. One way in which breast cancer cells are thought to accomplish this resistance to cell death is to activate Akt. Activated Akt can act through multiple pathways to promote resistance to cell death and is therefore considered to be a regulator of cancer cell survival.

While the molecular mechanisms by which Akt is activated are not well understood, recent research had determined that an oral HIV protease inhibitor drug, ritonavir, FDA approved to treat AIDS, exhibits activity against breast cancer in a mouse model of mammary cancer and blocks Akt activation (see, e.g., U.S. Publication No. 2007/0009593, incorporated by reference herein). Ritonavir is one example of an emerging approach to the treatment of cancer.

SUMMARY

Provided herein is a method of treating cancer comprising administering to a subject an effective amount of a compound of formula I:

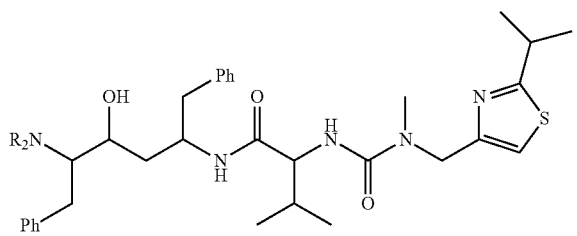

wherein each R is independently H or $C_{1-6}$ alkyl. In one embodiment, the compound of formula I is:

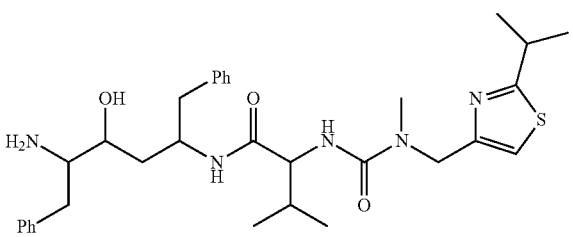

this compound is also known as desthiazolyl ritonavir (des-ritonavir or M1, as used herein). M1, for example, is used in the synthesis of ritonavir and is also a minor metabolite of ritonavir (see, e.g., Denissen, J. F. et al., *Drug Metabolism and Disposition* 25(4):489-501 (1997).) The compound of formula I may be more active as an inhibitor of cancer cell lines (e.g., breast cancer) than ritonavir (see Examples 1-7).

In some embodiments, the subject is a human. In certain embodiments, the subject is post-menopausal.

In some embodiments the cancer is selected from: bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer, and testicular cancer. In some embodiments, the cancer is breast cancer. In other embodiments, the breast cancer is selected from ER+ breast cancer, triple negative her2+ or her2− breast cancer.

In some embodiments, the subject has a cancer associated with resistance to a known anticancer drug regime. Such drug regimes, for example, can be selected from one or more of taxol, Herceptin, Avastin, fluouracil, and epirubicin. In other embodiments, the cancer comprises cells that express a P-glycoprotein (MDR), a multidrug resistance-associated protein (MRP), or a breast cancer resistance protein (BCRP).

Without being bound by theory, the compound of formula I may treat cancer through inhibition of a cytochrome P450, such as an epoxygenase (e.g., CYP3A4 or CYP3A5). In another embodiment, the compound of formula I may reduce the amount of one or more epoxyeicosatrienoic acids in at least one tumor cell of the subject relative to a tumor cell in a subject not administered a compound of formula I. In some embodiments, the epoxyeicosatrienoic acid is one or more of 5,6-epoxyeicosatrienoic acid; 8,9-epoxyeicosatrienoic acid; 11,12-epoxyeicosatrienoic acid; and 14,15-epoxyeicosatrienoic acid. In certain embodiments, the epoxyeicosatrienoic acid is 14(R),15(S)-epoxyeicosatrienoic acid or 14(S),15(R)-epoxyeicosatrienoic acid. In some embodiments, the compound of formula I reduces the amount of phosphorylated Akt in at least one tumor cell of the subject relative to a tumor cell in a subject not administered a compound of formula I. In other embodiments the compound of formula I inhibits Hsp90.

Further provided herein is a pharmaceutical composition comprising a compound of formula I, or a pharmaceutically acceptable salt form thereof. In some embodiments, the composition further comprises a carrier, excipient, or diluent (e.g., saline). In other embodiments, the composition further comprises a pain relief agent (e,g., a nonsteroidal anti-inflammatory drug (NSAID)), an antinausea agent, or an additional anticancer agent (e.g., paclitaxel, docetaxel, doxorubicin, liposomal doxorubicin, daunorubicin, epirubicin, fluorouracil, melphalan, cisplatin, carboplatin, irinotecan, cyclophosphamide, mitomycin-c, methotrexate, mitoxantrone, vinblastine, vincristine, vinorelbine, doxycycline, ifosfamide, teniposide, etoposide, bleomycin, leucovorin, taxol, Herceptin, Avastin, cytarabine, dactinomycin, interferon alpha, streptozocin, prednisolone, interleukin-2 (IL-2), fludarabine, rituximab, campath (anti-CD 52), 2-CDA, anastrozole (Arimidex), tamoxifen, fulvestrant, reloxifine, letrozole, toremifene, flutamide, leuprolide, or procarbazine). In some embodiments, the anticancer agent is paclitaxel, docetaxel, cisplatin, or irinotecan. In some embodiments, the composition further comprises ritonavir.

Also provided herein is a pharmaceutical composition comprising a compound of formula I and ritonavir, or a pharmaceutically acceptable salt form thereof. In some embodiments, the composition further comprises a carrier, excipient, or diluent. The ratio of the compound of formula I to ritonavir can be about 20:1. In some embodiments, the ratio of the compound of formula I to ritonavir can be about 2.75:1; about 2:1; or about 1.81:1.

A method of inducing apoptosis in a cell is provided herein, the method comprising contacting the cell with a therapeutically effective amount of a compound of formula I, or a pharmaceutically acceptable salt form thereof.

A method of reducing the amount of one or more of an epoxyeicosatrienoic acid, Hsp90, a cyclin, a cyclin dependent kinase, an ER, or her2 in a cell is also provided herein, the method comprising contacting the cell with a therapeutically effective amount of a compound of formula I, or a pharmaceutically acceptable salt form thereof.

Further provided herein is a method of inhibiting a cytochrome P450 in a cell, the method comprising contacting the cell with a therapeutically effective amount of a compound of formula I, or a pharmaceutically acceptable salt form thereof.

Also provided herein is a method of reducing the amount of phosphorylated Akt in a cell, the method comprising contacting the cell with a therapeutically effective amount of a compound of formula I, or a pharmaceutically acceptable salt form thereof.

A method of inhibiting Hsp90 in a cell is provided herein, the method comprising contacting the cell with a therapeutically effective amount of a compound of formula I, or a pharmaceutically acceptable salt form thereof.

Further provided herein is a method of treating cancer in a subject, the method comprising inhibiting CYP3A4 in the subject. A method of treating cancer in a subject, is also provided wherein the method comprises administering to the subject a pharmaceutical that inhibits CYP3A4.

Provided herein is a kit comprising a compound of formula I, or a pharmaceutically acceptable salt form thereof. In some embodiments, the kit further comprises instructions for treating a subject.

The details of one or more embodiments of the invention are set forth in the accompanying drawings and the description below. Other features, objects, and advantages of the invention will be apparent from the description and drawings, and from the claims.

DETAILED DESCRIPTION

I. Definitions

Figure 1A:
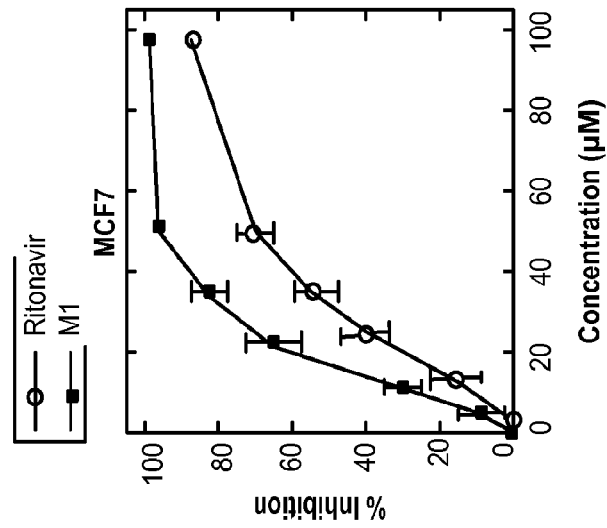
FIG. 1 illustrates inhibition of proliferation of the MCF7, T47D and MDA-MB-231 breast cancer cell lines using ritonavir and M1.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "administration" refers to delivery of a compound of formula I by any external route, including, without limitation, IV, intramuscular, SC, intranasal, inhalation, transdermal, oral, rectal, sublingual, and parenteral administration. It does not include the administration of a prodrug, i.e., any compound (whether itself active or inactive) that is converted chemically in vivo into a biologically active compound of formula I following administration of the prodrug to a patient. For example, administration, as used herein, does not include production of a compound of formula I via in vivo metabolism of ritonavir.

The term "contacting" means bringing at least two moieties together, whether in an in vitro system or an in vivo system.

The expression "effective amount," when used to describe an amount of compound applied in a method, refers to the amount of a compound that achieves the desired pharmacological effect or other effect, for example an amount that inhibits the abnormal growth or proliferation, or induces apoptosis of cancer cells, resulting in a useful effect.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

As used herein, "subject" (as in the subject of the treatment) means both mammals and non-mammals. Mammals include, for example, humans; non-human primates, e.g. apes and monkeys; cattle; horses; sheep; rats; mice; pigs; and goats. Non-mammals include, for example, fish and birds.

As used herein, "alkyl" carbon chains, if not specified, should be broadly interpreted, for example to encompass substituted or unsubstituted, straight, branched, unsaturated, and cyclic "chains."

II. Methods of Use

Provided herein are methods of treating cancer in a subject by administering to the subject a therapeutically effective amount of a compound of formula I:

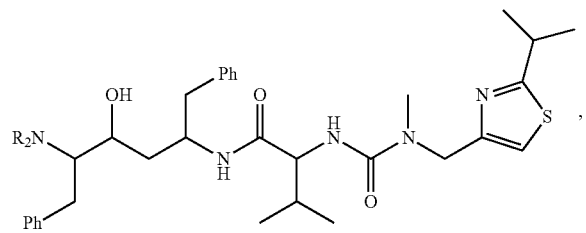

wherein each R is independently H or $C_{1-6}$ alkyl; or a pharmaceutically acceptable salt form thereof. In some embodiments, the compound of formula I is:

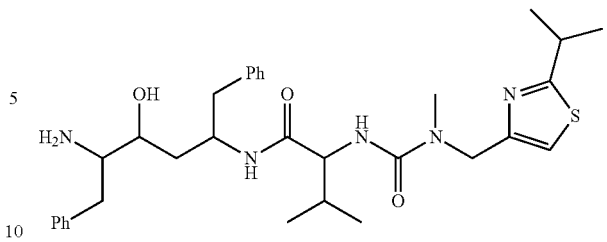

This compound is also known as desthiazolyl ritonavir or M1. Although all stereochemical species are contemplated in this application, in some embodiments, the compound according to formula I has the following structure:

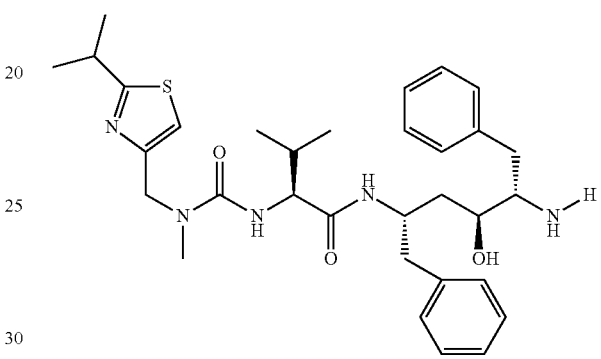

Non-limiting examples of cancers include bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer, and testicular cancer as well as leukemia and myeloma.

More particularly, cancers that may be treated by the compound, compositions and methods described herein include, but are not limited to, the following:

1) Breast cancers, including, for example $ER^+$ breast cancer, $ER^-$ breast cancer including triple negative breast cancer, her2$^-$ breast cancer, her2+ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative (her2$^-$). In some embodiments, the breast cancer is $ER^+$ or her2$^-$. In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; non-small cell lung cancer; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia.

11) Skin cancers, including, for example, malignant melanoma, basal cell carcinoma, squamous cell carcinoma, Kaposi's sarcoma, moles dysplastic nevi, lipoma, angioma, dermatofibroma, keloids, psoriasis.

12) Adrenal gland cancers, including, for example, neuroblastoma.

In certain embodiments, the cancer is breast cancer. In some embodiments, the breast cancer is selected from $ER^+$ breast cancer, $ER^-$ breast cancer, her2+ breast cancer, her2$^-$ breast cancer, and triple negative breast cancer.

Cancers may be solid tumors that may or may not be metastatic. Cancers may also occur, as in leukemia, as a diffuse tissue. Thus, the term "tumor cell," as provided herein, includes a cell afflicted by any one of the above identified disorders. In some embodiments, a subject may have cancer (e.g., breast cancer, lymphoma, HD, or leukemia) and increased cardiac risk factors, such as those for whom anthracycline is not an appropriate treatment.

In some embodiments, the subject is a human. In certain embodiments, the subject is a female human. In other embodiments, the subject is post-menopausal. In some embodiments, the subject is a male human.

In some embodiments, the subject has a cancer associated with resistance to a known anticancer drug regime, e.g., wherein the cancer comprises cells that express a P-glycoprotein (MDR), a multidrug resistance-associated protein (MRP), or a breast cancer resistance protein (BCRP). In certain embodiments the anticancer drug regime is selected from one or more of Taxol, Abraxane, Herceptin, Avastin, fluorouracil, and epirubicin. Also the anticancer drug regime could include statin drugs.

A method of treating cancer using a compound of formula I may be combined with existing methods of treating cancers, for example by chemotherapy, irradiation, or surgery (e.g., oophorectomy). In certain embodiments, a compound of formula I can be used as a radiation sensitizer in the treatment of head and neck cancer, lung cancer, and glioma (see, e.g., Gupta, A. and Mueschel, R. *Cancer Res.* 65(18):8256-8265 (2005)). In some embodiments, a compound of formula I can be administered before, during, or after another anticancer agent or treatment.

In some embodiments (e.g., when compositions comprising a compound of formula I are administered in conjunction with another pharmaceutical (e.g. an anticancer agent or ritonavir), one can create a synergistic effect among the agents administered and thereby improve the outcome for a patient. In some embodiments, a compound of formula I (or a pharmaceutically acceptable salt form thereof) can be administered in combination with (i.e., before, during, or after) administration of a pain relief agent (e.g., a nonsteroidal anti-inflammatory drug such as celecoxib or rofecoxib), an antinausea agent, or an additional anticancer agent (e.g., paclitaxel, docetaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, Herceptin, Avastin, Abraxane, cytarabine, dactinomycin, interferon alpha, streptozocin, prednisolone, irinotecan, gemcitabine, pemetrexed, sulindac, 5-fluorouracil, capecitabine or procarbazine). In certain embodiments, the anticancer agent is paclitaxel or docetaxel. In other embodiments, the anticancer agent is cisplatin or irinotecan.

Non-limiting examples of combination therapies include the following. In the treatment of her2+ breast cancer, for example, a compound of formula I can be administered in combination with Herceptin or Tykerb. In the treatment of lung cancer, head and neck cancer, colon cancer, and breast cancer, for example, a compound of formula I can be administered in combination with cetuximab, erlotinib, or gefitinib. In the treatment of colon cancer, for example, a compound of formula I can be administered in combination with Avastin or Folfox combination. In the treatment of prostate cancer, for example, a compound of formula I can be administered in combination with docetaxel. In the treatment of breast cancer, for example, a compound of formula I can be administered in combination with Abraxane. In the treatment of renal cancer, for example, a compound of formula I can be administered in combination with sorafenib, sunitinib, or temsirolimus. In the treatment of melanoma or glioma, for example, a compound of formula I can be administered in combination with temozolomide. In the treatment of mantle cell lymphoma or myeloma, for example, a compound of formula I can be administered in combination with Velcade. In the treatment of diffuse large B cell lymphoma, for example, a compound of formula I can be administered in combination with rituximab-CHOP therapy (cyclophosphamide, doxorubicin, vincristine, and prednisone). In the treatment of chronic myelogenous leukemia, for example, a compound of formula I can be administered in combination with imatinib or dasatinib. In the treatment of epithelial malignancies, for example, a compound of formula I can be administered in combination with ketoconazole or itraconazole.

In some embodiments, a compound of formula I can be combined with an HIV protease inhibitor, such as those that function in non-cross resistant mechanisms (e.g., nelfinavir). In another embodiment, a compound of formula I can be combined with a drug that is not metabolized though CYP3A, e.g., gemcitabine. In other embodiments, a compound of formula I may be combined with a hormonal therapy, e.g., tamoxifen, fulvestrant, gosereline, and exemestane.

In some embodiments, a compound of formula I is combined with ritonavir. In some embodiments, the ratio of a compound of formula I to ritonavir can be about 20:1 (e.g., about 18:1; about 16:1; about 15.5:1; about 15:1; about 12:1; about 11.75:1; about 10:1; about 8:1; about 7.25:1; about 6:1; about 5:1; about 4.6:1; about 4:1; about 3:1; about 2.75:1; about 2.5:1; about 2:1; about 1.8:1; about 1.75:1; about 1.5:1; about 1.25:1; and about 1:1). In some embodiments, the ratio of a compound of formula I to ritonavir is about 2.75:1. In some embodiments, the ratio is about 2:1. In some embodiments, the ratio is about 1.8:1. In some embodiments, the ratio of a compound of formula I to ritonavir can be about 1:20 (e.g., about 1:18; about 1:16; about 1:15.1; about 1:15; about 1:12; about 1:11.75; about 1:10; about 1:8; about 1:7.25; about 1:6; about 1:5; about 1:4.6; about 1:4; about 1:3; about 1:2.75; about 1:2.5; about 1:2; about 1:1.5).

In some embodiments, a compound of formula I can be administered with a statin drug, acetylsalicylic acid, an imid drug (e.g., revlimid), an Hsp90 inhibitor (e.g., 17-AAG), and/or any drug currently in clinical development for the treatment of cancer (e.g., vitamin D3).

In a further embodiment, a compound of formula I can be administered, for example, in combination with dose dense therapies, such as CALGB 9741 adriamycin/cytoxan followed by taxol (see, e.g., *J. Clin. Oncol.* 21(8): 1431-143 (2003)), taxotere/cytoxan (see, e.g., *J. Clin. Oncol.* 24(34): 1673-1684 (2006)), NSABP B31/NCCTG 9831 Herceptin regimen for her2+ breast cancer (see, e.g., *N. Engl. J. Med.* 353(16):1673-1684 (2005)), and paclitaxel or docetaxel and Avastin or navelbine.

In some embodiments, administration of a compound of formula I and an additional therapeutic agent can produce a synergistic effect. This effect can be demonstrated through the development of a combination index (CI). In certain embodiments, the index can be calculated as a function of the fraction of cells affected according to the procedure of Chou and Talalay, *Advance Enz. Regul.* (1985) 22: 27-55. This is a well-known test that evaluates coefficient interactions against a range of cell death proportions. For example, if treatment with drug A results in 30% cell death and treatment with drug B results in 50% cell death, than it would be expected that the combination of the two drugs would result in 65% cell death. Accordingly, if the ratio of the predicted cell death to that measured upon combination of the drugs is less than one, then a synergistic effect is observed.

A method of inhibiting a cytochrome P450 in a cell is also provided herein, the method comprising contacting the cell with a therapeutically effective amount of a compound of formula I. In some embodiments, the cytochrome P450 is an epoxygenase. In certain embodiments, the epoxygenase is selected from the CYP3A subfamily (e.g., CYP3A4 and CYP3A5). In some embodiments, the epoxygenase is CYP3A4. In other embodiments, the cytochrome P450 is selected from the CYP1A subfamily, CYP1B subfamily, CYP2C subfamily (e.g., CYP2C8 and CYP2C9), CYP2J2, CYP4F subfamily, CYP4A subfamily and CYP19A1. The method of inhibiting cytochrome P450 in a cell may be performed by contacting the cell with a compound according to formula I, or a pharmaceutically acceptable salt form thereof, in vitro, thereby inducing inhibition of cytochrome P450 of a cell in vitro. Uses of such an in vitro method of inhibiting cytochrome P450 include, but are not limited to use in a screening assay (for example, wherein a compound according to formula I is used as a positive control or standard compared to compounds of unknown activity or potency in inhibiting cytochrome P450). In some embodiments thereof, cytochrome P450 is inhibited in a cancer cell. See Examples 10-15.

Inhibition of a cytochrome P450 can be determined by, for example, incubating CYP3A4 or CYP3A5 Supersomes™ with cytochrome b5, and 5 µM arachidonic acid (AA) with or without NADPH. The minus NADPH reactions can be used as a control for AA oxidation. By measurement of epoxyeicosatrienoic acid products using electron capture APCI MS/MS, it can be determined whether CYP3A4 or CYP3A5 synthesis of epoxyeicosatrienoic acid regio- and stereoisomers is inhibited by a compound of formula I. In another example, inhibition of CYP2C8, CYP2D6 and CYP2J2 can be tested using model pharmacologic substrates (e.g., astemizole and ebastine for 2J2).

The method of inhibiting cytochrome P450 in a cell may be performed, for example, by contacting a tumor cell with a compound according to formula I, in vivo, thereby inhibiting a cytochrome P450 in a subject in vivo. The contacting is achieved by causing a compound according to formula I, or a pharmaceutically acceptable salt form thereof, to be present in the subject in an amount effective to achieve inhibition of the cytochrome P450. This may be achieved, for example, by administering an effective amount of a compound according to formula I, or a pharmaceutically acceptable salt form thereof, to a subject. Uses of such an in vivo method of inhibiting a cytochrome P450 include, but are not limited to use in methods of treating a disease or condition, wherein inhibiting of the cytochrome P450 is beneficial. In some embodiments thereof, the cytochrome P450 is inhibited in a cancer cell, for example in a patient suffering from cancer. The method is preferably performed by administering an effective amount of a compound according to formula I, or a pharmaceutically acceptable salt form thereof, to a subject who is suffering from cancer.

Also provided herein is a method of treating cancer in a subject, the method comprising inhibiting CYP3A4 in the subject. In some embodiments, a method of treating cancer in a subject can include administering to the subject a pharmaceutical that inhibits CYP3A4. As above, the methods can be performed in vivo or in vitro and includes contacting a cell (e.g., a cancer cell) with a pharmaceutical capable of inhibiting CYP3A4. In some embodiments, the pharmaceutical is a compound according to formula I, or a pharmaceutically acceptable salt form thereof.

Further provided herein is a method of inducing cell cycle arrest and/or apoptosis in a cell. The method includes contacting the cell with a therapeutically effective amount of a compound of formula I, or a pharmaceutically acceptable salt form thereof. The method of inducing cell-cycle arrest and/or apoptosis of a cell may be performed by contacting the cell with a compound according to formula I, or a pharmaceutically acceptable salt form thereof, in vitro, thereby inducing cell-cycle arrest and/or apoptosis of a cell in vitro. Uses of such an in vitro method of inducing cell-cycle arrest and/or apoptosis include, but are not limited to use in a screening assay (for example, wherein a compound according to formula I is used as a positive control or standard compared to compounds of unknown activity or potency in inducing cell-cycle arrest and/or apoptosis). In some embodiments thereof, the cell-cycle arrest and/or apoptosis is induced in a cancer cell.

Induction of apoptosis can be determined using the Annexin V-FITC/PI apoptosis detection kit (Oncagene, Boston, Mass.). For example, after plating at $5\times10^5$ in a 100-mm plate, cancer cells can be grown for 48 hours in complete medium in presence of a drug, including a compound or formula 1, and a control, such as vehicle (DMSO). The culture and drug exposure conditions for the apoptosis assays can be done across a range of 5 to 60 µmol/L drug. Cells can be harvested by trypsin treatment, washed with complete medium to neutralize the trypsin, and stained with PI and Annexin V-FITC. The events can then be analyzed using FACScan analysis and CellQuest software (Becton Dickinson). See Example 2.

The method of inducing cell-cycle arrest and/or apoptosis of a cell may be performed, for example, by contacting a tumor cell with a compound according to formula I, in vivo, thereby inducing cell-cycle arrest and/or apoptosis in a subject in vivo. The contacting is achieved by causing a compound according to formula I, or a pharmaceutically acceptable salt form thereof, to be present in the subject in an amount effective to achieve cell-cycle arrest and/or apoptosis. This may be achieved, for example, by administering an effective amount of a compound according to formula I, or a pharmaceutically acceptable salt form thereof, to a subject. Uses of such an in vivo method of inducing cell-cycle arrest and/or apoptosis include, but are not limited to use in methods of treating a disease or condition, wherein inducing cell-cycle arrest and/or apoptosis is beneficial. In some embodiments thereof, the cell-cycle arrest and/or apoptosis is induced in a cancer cell, for example in a patient suffering from cancer. The method is preferably performed by administering an effective amount of a compound according to formula I, or a pharmaceutically acceptable salt form thereof, to a subject who is suffering from cancer.

A method of reducing the amount of one or more of an epoxyeicosatrienoic acid, Hsp90, a cyclin, a cyclin dependent kinase, an ER, or her2 in a cell is provided herein, the method comprising contacting the cell with a therapeutically effective amount of a compound of formula I. The amount of one or more of an epoxyeicosatrienoic acid, Hsp90, a cyclin, a cyclin dependent kinase, an ER, or her2 in the treated cell is reduced relative to a cell in a subject not administered a compound of formula I. In some embodiments, an epoxyeicosatrienoic acid is selected from 5,6-epoxyeicosatrienoic acid; 8,9-epoxyeicosatrienoic acid; 11,12-epoxyeicosatrienoic acid; 14,15-epoxyeicosatrienoic acid; and mixtures thereof. An epoxyeicosatrienoic acid may exist as either of two stereoisomers, e.g., 14(R),15(S)-epoxyeicosatrienoic acid or 14(S),15(R)-epoxyeicosatrienoic acid. The method of reducing the amount of one or more of an epoxyeicosatrienoic acid, Hsp90, a cyclin, a cyclin dependent kinase, an ER, or her2 in a cell may be performed by contacting the cell with a compound according to formula I, or a pharmaceutically acceptable salt form thereof, in vitro, thereby reducing the amount of one or more of an epoxyeicosatrienoic acid, Hsp90, a cyclin, a cyclin dependent kinase, an ER, or her2 of a cell in vitro. Uses of such an in vitro method of reducing the amount of one or more of an epoxyeicosatrienoic acid, Hsp90, a cyclin, a cyclin dependent kinase, an ER, or her2 include, but are not limited to use in a screening assay (for example, wherein a compound according to formula I is used as a positive control or standard compared to compounds of unknown activity or potency in reducing the amount of one or more epoxyeicosatrienoic acids). In some embodiments thereof, the amount of one or more epoxyeicosatrienoic acids is reduced in a cancer cell.

The method of reducing the amount of one or more of an epoxyeicosatrienoic acid, Hsp90, a cyclin, a cyclin dependent kinase, an ER, or her2 in a cell may be performed, for example, by contacting a cell, e.g., a tumor cell, with a compound according to formula I, in vivo, thereby reducing the amount of one or more epoxyeicosatrienoic acids in the cell in vivo. The contacting is achieved by causing a compound according to formula I, or a pharmaceutically acceptable salt form thereof, to be present in a subject in an amount effective to achieve a reduction in the amount of one one or more of an epoxyeicosatrienoic acid, Hsp90, a cyclin, a cyclin dependent kinase, an ER, or her2. This may be achieved, for example, by administering an effective amount of a compound according to formula I, or a pharmaceutically acceptable salt form thereof, to a subject. Uses of such an in vivo method of reducing the amount of one or more epoxyeicosatrienoic acids include, but are not limited to use in methods of treating a disease or condition, wherein reduction in the amount of one or more epoxyeicosatrienoic acids is beneficial. In some embodiments thereof, the amount of one or more of an epoxyeicosatrienoic acid, Hsp90, a cyclin, a cyclin dependent kinase, an ER, or her2 is reduced in a cancer cell, for example in a patient suffering from cancer. The method is preferably performed by administering an effective amount of a compound according to formula I, or a pharmaceutically acceptable salt form thereof, to a subject who is suffering from cancer.

Further provided herein is a method of reducing the amount of phosphorylated Akt (pAkt) in a cell, the method comprising contacting the cell with a therapeutically effective amount of a compound of formula I. The amount of pAkt in the treated cell is reduced relative to a cell in a subject not administered a compound of formula I. The method of reducing the amount of pAkt in a cell may be performed by contacting the cell with a compound according to formula I, or a pharmaceutically acceptable salt form thereof, in vitro, thereby reducing the amount of pAkt of a cell in vitro. Uses of such an in vitro method of reducing the amount of pAkt include, but are not limited to use in a screening assay (for example, wherein a compound according to formula I is used as a positive control or standard compared to compounds of unknown activity or potency in reducing the amount of pAkt). In some embodiments thereof, the amount of pAkt is reduced in a cancer cell.

The method of reducing the amount of pAkt in a cell may be performed, for example, by contacting a cell, e.g., a tumor cell, with a compound according to formula I, in vivo, thereby reducing the amount of pAkt in a cell in vivo. The contacting is achieved by causing a compound according to formula I, or a pharmaceutically acceptable salt form thereof, to be present in a subject in an amount effective to achieve a reduction in the amount of pAkt. This may be achieved, for example, by administering an effective amount of a compound according to formula I, or a pharmaceutically acceptable salt form thereof, to a subject. Uses of such an in vivo method of reducing the amount of pAkt include, but are not limited to use in methods of treating a disease or condition, wherein reduction in the amount of pAkt is beneficial. In some embodiments thereof, the amount of phosphorylated Akt is reduced in a cancer cell, for example in a patient suffering from cancer. The method is preferably performed by administering an effective amount of a compound according to formula I, or a pharmaceutically acceptable salt form thereof, to a subject who is suffering from cancer.

Reduction of phosphorylated Akt can be evaluated, for example, by a Western blot of cells treated with a compound of formula I for 24 and 48 h and evaluating for Akt/pAkt. Student's t-test can be used to assess differences in total Akt and pAkt, comparing a compound of formula I, vehicle treated cells (e.g., DMSO), and other anticancer agents (e.g., ritonavir). Any appropriate cell line may be used, for example, any of the NCI 60 cell lines, such as MCF7, T47D, MDA-MB-231 and MDA-MB-436.

A method of inhibiting Hsp90 in a cell is also provided herein, the method comprising contacting the cell with a therapeutically effective amount of a compound of formula I. The method of inhibiting Hsp90 in a cell may be performed by contacting the cell with a compound according to formula I, or a pharmaceutically acceptable salt form thereof, in vitro, thereby inducing inhibition of Hsp90 of a cell in vitro. Uses of such an in vitro method of inhibiting Hsp90 include, but are not limited to use in a screening assay (for example, wherein a compound according to formula I is used as a positive control or standard compared to compounds of unknown activity or potency in inhibiting Hsp90). In some embodiments thereof, Hsp90 is inhibited in a cancer cell.

The method of inhibiting Hsp90 in a cell may be performed, for example, by contacting a cell, e.g., a tumor cell, with a compound according to formula I, in vivo, thereby inhibiting Hsp90 in a subject in vivo. The contacting is achieved by causing a compound according to formula I, or a pharmaceutically acceptable salt form thereof, to be present in a subject in an amount effective to achieve inhibition of Hsp90. This may be achieved, for example, by administering an effective amount of a compound according to formula I, or a pharmaceutically acceptable salt form thereof, to a subject. Uses of such an in vivo method of inhibiting Hsp90 include, but are not limited to use in methods of treating a disease or condition, wherein inhibiting of Hsp90 is beneficial. In some embodiments thereof, Hsp90 is inhibited in a cancer cell, for example in a patient suffering from cancer. The method is preferably performed by administering an effective amount of a compound according to formula I, or a pharmaceutically acceptable salt form thereof, to a subject who is suffering from cancer.

Inhibition of Hsp90 can be evaluated by surface plasmon resonance studies of a compound of formula I, using a CM-5 Biacore chip on which Hsp90 (Stressgen, Ann Arbor) has been immobilized. This method can also be used to evaluate the chaperoning activity of a compound of formula I by evaluation of luciferase refolding. See Examples 4 and 9.

Further provided herein is a method of increasing the amount of reactive oxygen species (ROS) in a cell, the method comprising contacting the cell with a therapeutically effective amount of a compound of formula I. The amount of ROS in the treated cell is increased relative to a cell in a subject not administered a compound of formula I. The method of increasing the amount of ROS in a cell may be performed by contacting the cell with a compound according to formula I, or a pharmaceutically acceptable salt form thereof, in vitro, thereby increasing the amount of ROS of a cell in vitro. Uses of such an in vitro method of increasing the amount of oxygen species include, but are not limited to use in a screening assay (for example, wherein a compound according to formula I is used as a positive control or standard compared to compounds of unknown activity or potency in increasing the amount of ROS). In some embodiments thereof, the amount of ROS is increased in a cancer cell.

The method of increasing the amount of ROS in a cell may be performed, for example, by contacting a cell, e.g., a tumor cell, with a compound according to formula I, in vivo, thereby increasing the amount of ROS in a subject in vivo. The contacting is achieved by causing a compound according to formula I, or a pharmaceutically acceptable salt form thereof, to be present in a subject in an amount effective to achieve an increase in the amount of ROS. This may be achieved, for example, by administering an effective amount of a compound according to formula I, or a pharmaceutically acceptable salt form thereof, to a subject. Uses of such an in vivo method of increasing the amount of ROS include, but are not limited to use in methods of treating a disease or condition, wherein an increase in the amount of ROS is beneficial. In some embodiments thereof, the amount of ROS is increased in a cancer cell, for example in a patient suffering from cancer. The method is preferably performed by administering an effective amount of a compound according to formula I, or a pharmaceutically acceptable salt form thereof, to a subject who is suffering from cancer.

Production of ROS can be analyzed using flow cytometry. For example, induction of ROS, including peroxide and superoxide, can be studied in cancer cell line. Cells can be seeded in 6 well plates (~80,000 cells/well) using the appropriate medium, and exposed to a drug for 24 hours. Subsequently, the medium can be removed from the wells and the cells can then be exposed to DHE (2 μM in PBS) or Carboxy-H2-DCFDA (10 μM in PBS) for 30 minutes. Cells can then be trypsinized, washed two times with PBS and analyzed by flow cytometry. Additional cells can be exposed to $H_2O_2$ (250 μM) for 2 hours as a positive control for ROS production. See Example 3.

III. Pharmaceutical Compositions

Provided herein is a compound of formula I:

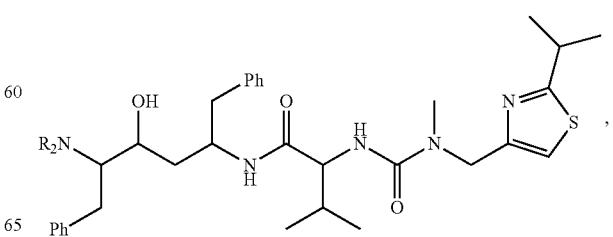

wherein each R is independently H or $C_{1-6}$ alkyl; or a pharmaceutically acceptable salt form thereof. In some embodiments, the compound of formula I is:

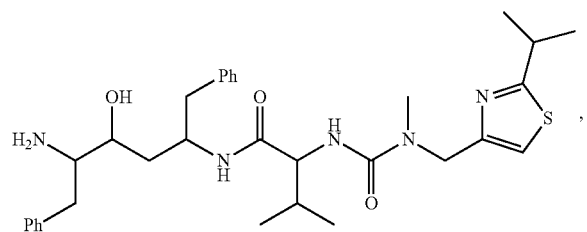

and pharmaceutically acceptable salt forms thereof. This compound is also known as desthiazolyl ritonavir (desritonavir or M1) is a minor metabolite of ritonavir. Ritonavir is a known agent in the treatment of HIV and its use as an anticancer agent has been studied (see, e.g., U.S. Publication No. 2007/0009593, incorporated herein by reference). A compound of formula I can be synthesized using conventional techniques using readily available starting materials. In general, a compound of formula I is conveniently obtained via standard organic chemistry synthesis methods. For example, two such methods are described in U.S. Pat. Nos. 5,616,720 and 6,407,252.

Although all stereochemical species are contemplated in this application, in some embodiments, the compound according to formula I has the following structure:

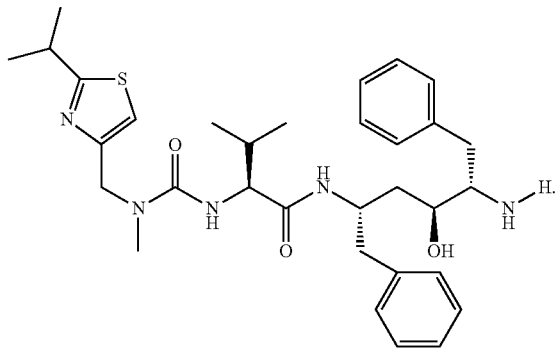

The term "pharmaceutically-acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification or formulation of compounds described herein. In general the useful properties of the compounds described herein do not depend critically on whether the compound is or is not in a salt form, so unless clearly indicated otherwise (such as specifying that the compound should be in "free base" or "free acid" form), reference in the specification to a compound of formula I should be understood as encompassing salt forms of the compound, whether or not this is explicitly stated.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, methanesulfonic acid, galactaric and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound according to formula I by reacting, for example, the appropriate acid or base with a compound according to formula I. Preferably the salts are in crystalline form, and preferably prepared by crystallization of the salt from a suitable solvent. A person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

Provided herein are pharmaceutical compositions comprising a compound of formula I. The pharmaceutical compositions provided herein contain a compound of formula I in an amount that is useful in the treatment of cancer.

In some embodiments, the pharmaceutical composition further comprises a pharmaceutically acceptable carrier, excipient, or diluent. Pharmaceutical carriers suitable for administration of the compounds provided herein include any such carriers known to those skilled in the art to be suitable for the particular mode of administration. Pharmaceutically acceptable carriers, excipients, and diluents include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as .alpha.-, .beta., and .gamma.-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. In some embodiments, the carrier, excipient, or diluent is a physiologically acceptable saline solution.

The compounds according to formula I can also be administered in combination with existing methods of treating cancers, for example by chemotherapy, irradiation, or surgery. In some embodiments, a compound of formula I can be administered before, during, or after another anticancer agent or treatment. In some embodiments (e.g., when compositions comprising a compound of formula I are administered in conjunction with another anticancer agent or ritonavir), one can create a synergistic effect among the agents administered and thereby improve the outcome for a patient. In some embodiments, a compound of formula I (or a pharmaceutically acceptable salt form thereof) can be administered in combination with (i.e., before, during, or after) administration of a pain relief agent (e.g., a nonsteroidal anti-inflammatory drug such as celecoxib or rofecoxib), an antinausea agent, anti-diarrheal or an additional anticancer agent (e.g., paclitaxel, docetaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, taxol, Herceptin, Avastin, cytarabine, dactinomycin, interferon alpha, streptozocin, prednisolone, irinotecan, sulindac, 5-fluorouracil, capecitabine or procarbazine). In certain embodiments, the anticancer agent is paclitaxel or docetaxel. In other embodiments, the anticancer agent is cisplatin or irinotecan. In some embodiments, a compound of formula I is administered in combination with (i.e., before, during, or after) ritonavir.

Also provided herein is a pharmaceutical composition comprising a compound of formula I and ritonavir, or a pharmaceutically acceptable salt form thereof. In some embodiments, the composition further comprises a carrier, excipient, or diluent. The ratio of the compound of formula I to ritonavir can be about 20:1 (e.g., about 18:1; about 16:1; about 15.5:1; about 15:1; about 12:1; about 11.75:1; about 10:1; about 8:1; about 7.25:1; about 6:1; about 5:1; about 4.6:1; about 4:1; about 3:1; about 2.75:1; about 2.5:1; about 2:1; about 1.8:1; about 1.75:1; about 1.5:1; about 1.25:1; and about 1:1). In some embodiments, the ratio of the compound of formula I to ritonavir can be about 2.75:1; about 2:1; or about 1.81:1.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., Ansel Introduction to Pharmaceutical Dosage Forms, Fourth Edition 1985, 126).

The concentration of a compound of formula I in a pharmaceutical composition will depend on absorption, inactivation and excretion rates of the compound, the physicochemical characteristics of the compound, the dosage schedule, and amount administered as well as other factors known to those of skill in the art. For example, the amount that is delivered is sufficient to treat $ER^+$ breast cancer, as described herein. In another embodiment, the amount that is delivered is sufficient to treat triple negative breast cancer.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Absolute bioavailability can be determined by measuring the AUC achieved with a particular dosage form and route of administration as compared to that of an IV dosage form of a solubilized formulation of the drug. A poorly bioavailable drug has an absolute bioavailability that is less than about 30% (e.g., less than about 25%; less than about 20%; less than about 15%; less than about 10%; and less than about 5%) of the IV dosage form of the drug. On the other hand, a drug can have an acceptable bioavailability if it can measure an absolute bioavailability of greater than about 30% (e.g., greater than about 35%; greater than about 40%; greater than about 45%; greater than about 50%; greater than about 55%; greater than about 60%; greater than about 65%; greater than about 70%; greater than about 75%; greater than about 80%; greater than about 85%; greater than about 90%; and greater than about 95%) as compared to an IV dosage form of the drug. In some embodiments, an oral formulation of a compound according to formula I can have an absolute bioavailability of greater than about 30%.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing a compound of formula I in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

IV. Kits

Also provided herein are kits. Typically, a kit includes a compound of formula I. In certain embodiments, a kit can include one or more delivery systems, e.g., for a compound of formula I, and directions for use of the kit (e.g., instructions for treating a subject). In certain embodiments, a kit can include a compound of formula I and one or more additional anticancer agents. In another embodiment, a kit can include a compound of formula I and one or more antinausea agents. In some embodiments, the kit can include a compound of formula I and one or more pain relief agents. In some embodiments, the kit can include a compound of formula I and ritonavir. In some embodiments, the kit can include a compound of formula I and a label that indicates that the contents are to be administered to a subject resistant to an anticancer agent, such as Herceptin. In another embodiment, the kit can include a compound of formula I and a label that indicates that the contents are to be administered to a subject with cells expressing a P-glycoprotein (MDR), a multidrug resistance-associated protein (MRP), or a breast cancer resistance protein (BCRP). In another embodiment, the kit can include a compound of formula I and a label that indicates that the contents are to be administered to a subject with ER⁻ breast cancer. In another embodiment, the kit can include a compound of formula I and a label that indicates that the contents are to be administered to a subject with her2⁻ breast cancer. In a further embodiment, a kit can include a compound of formula I and a label that indicates that the contents are to be administered with an anticancer agent. In another embodiment, a kit can include a compound of formula I and a label that indicates that the contents are to be administered with an antinausea agent. In some embodiments, a kit can include a compound of formula I and a label that indicates that the contents are to be administered with a pain relief agent. In a further embodiment, a kit can include a compound of formula I and a label that indicates that the contents are to be administered with ritonavir.

EXAMPLES

Example 1

M1 Inhibits Breast Cancer Cell Proliferation

Figure 1B:
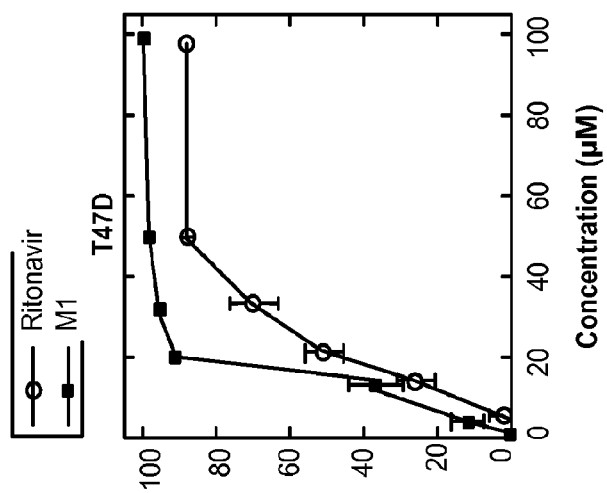
Figure 1C:
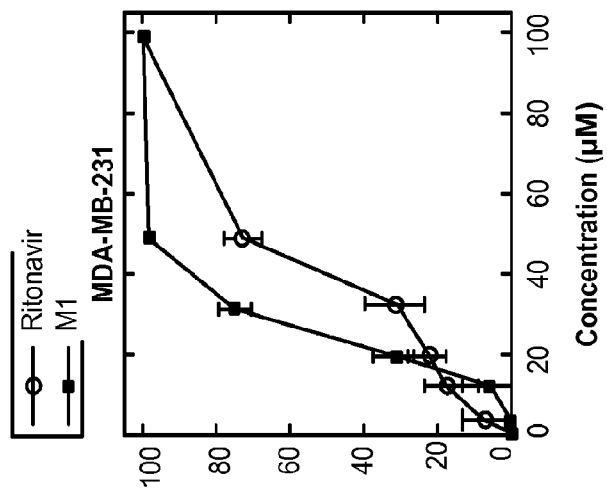

M1 inhibition of proliferation of MCF7, T47D and MDA-MB-231 cell lines was studied. Cells (n=2000/well) were seeded in 96 well plates with drug or vehicle (DMSO) on D1 and after 48 h the cell number was determined by MTT assay. Each assay was performed with 8 measurements for each data point (See FIG. 1, wherein graph A corresponds to MCF7, graph B corresponds to T47D, and graph C corresponds to MDA-MB-231).

The MCF7-her2 line, over-expressing the her2 oncoprotein, exhibited an identical $IC_{50}$ of 25 µM for ritonavir and M1, suggesting that her2 can overcome the added efficacy of M1 and may promote a mechanism of resistance to the compound of formula I. The $IC_{50}$ of M1 for the non-transformed human breast epithelial line MCF10A is 50 µM, indicating greater selective toxicity of M1 for transformed cell line relative to nontransformed cell lines compared to ritonavir, which exhibits an $IC_{50}$ for MCF10A of 35 µM. Remarkably, M1 does not inhibit HIV replication in an MT-4 cell based assay (see, e.g., Denissen, J. F. et al., *Drug Metabolism and Disposition: The Biological Fate of Chemicals* 25: 489-501 (1997)). Preliminary flow cytometry apoptosis studies of the MCF7 line treated with M1 (45 µM) exhibit two-fold higher concentration of early apoptotic cells with M1 (28%) compared to iso-dosed ritonavir (14%), suggesting that M1 is a more efficient inducer of apoptosis. In addition, the $IC_{90}$ values for the ER⁺ lines are more than 30 µM less than ritonavir, suggesting that M1 is capable of a higher fractional cell kill.

Example 2

Apoptosis Induced by Administration of MI

Induction of apoptosis was studied in a MCF7 breast cancer cell line. Apoptotic cells were detected using an Annexin V-FITC/PI apoptosis detection kit (Oncagene, Boston, Mass.). After plating at $5\times10^5$ in a 100-mm plate, the cells were grown for 48 hours in complete medium in presence of M1, ritonavir, or vehicle (DMSO). The culture and drug exposure conditions for the apoptosis assays were done across a range of 5 to 60 µmol/L M1 and ritonavir. Cells were harvested by trypsin treatment, washed with complete medium to neutralize the trypsin, and stained with PI and Annexin V-FITC. A total of $1\times10^4$ events were analyzed per assay by FACScan analysis using CellQuest software (Becton Dickinson). Replicate assays were done to confirm the results.

Figure 2:
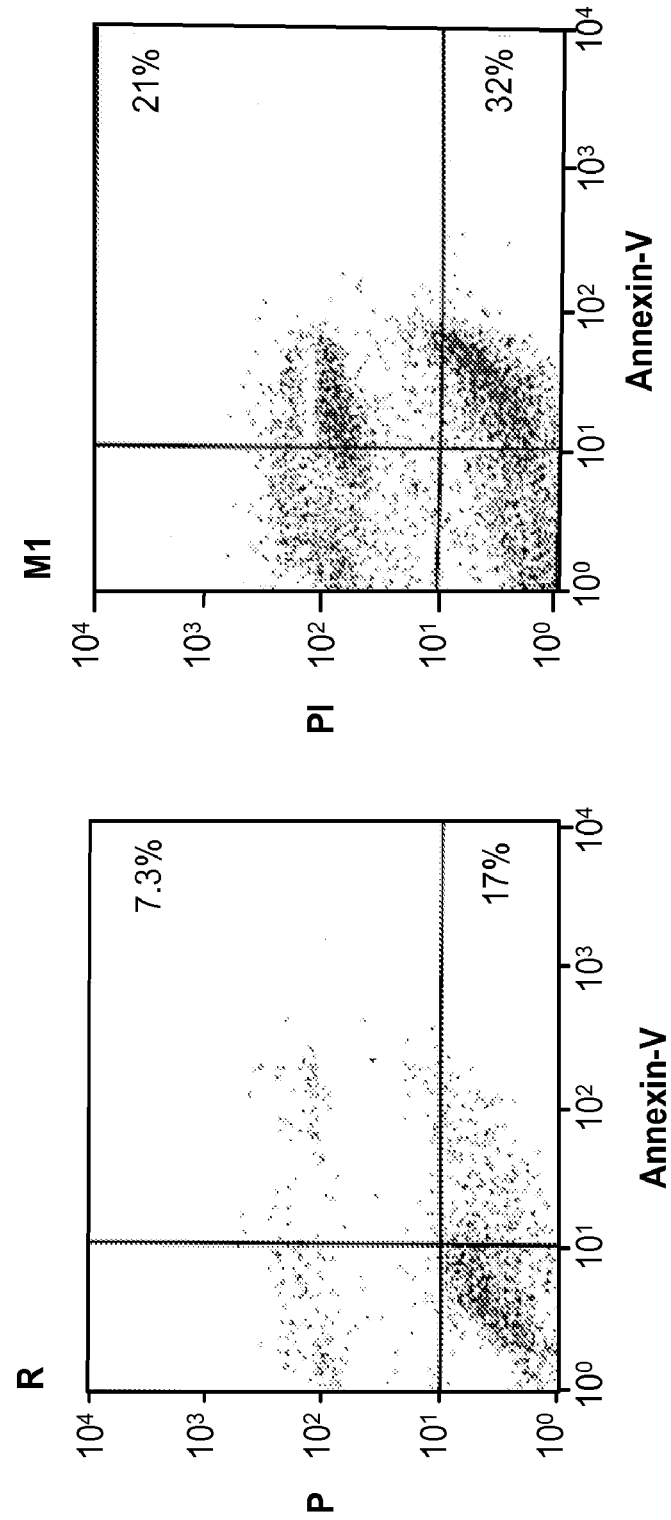
FIG. 2 shows desthiazolyl ritonavir (M1) induces apoptosis more potently than ritonavir in the MCF7 line.

FIG. 2 compares the induction of apoptosis of ritonavir (R) and M1. Early apoptotic cells are exhibited in the lower right quadrant and were compared with treatment at the ritonavir $IC_{50}$ (30 µM) resulting in a significantly higher fraction of apoptotic cells for M1 versus ritonavir (32 vs. 17%).

As FIG. 2 and the tables below illustrate, M1 is a more potent inducer of apoptosis than ritonavir.

TABLE 1

M1 and ritonavir compared below the $IC_{50}$ for both drugs.

|  | LR % Early Apoptosis | UR % Late Apoptosis |
| --- | --- | --- |
| DMSO vehicle | 3.35 | 5.93 |
| Ritonavir | 14.12 | 23.0 |
| M1 | 27.46 | 34.74 |

Ritonavir and M1 are compared at 45 µM.

TABLE 2

M1 and ritonavir compared at the M1 $IC_{50}$ for MCF7

|  | LR % Early Apoptosis | UR % Late Apoptosis |
| --- | --- | --- |
| DMSO vehicle | 9.26 | 6.56 |
| Ritonavir | 13.83 | 11.16 |
| M1 | 9.42 | 10.73 |

Ritonavir and M1 are compared at 15 µM.

TABLE 3

M1 and ritonavir compared at the ritonavir IC$_{50}$ for MCF7

|  | LR % Early Apoptosis | UR % Late Apoptosis |
|---|---|---|
| DMSO vehicle | 7.17 | 5.11 |
| Ritonavir | 15.11 | 7.95 |
| M1 | 39.74 | 20.00 |

Ritonavir and M1 are compared at 30 μM.

TABLE 4

M1 and ritonavir compared above the IC$_{50}$ for both drugs

|  | LR % Early Apoptosis | UR % Late Apoptosis |
|---|---|---|
| DMSO vehicle | 6.86 | 3.74 |
| Ritonavir | 17.10 | 7.30 |
| M1 | 31.95 | 21.31 |

Ritonavir and M1 are compared at 45 μM.

A similar study was performed using T47D (ER+), MDA-MB-231 (triple negative) and SKBR3 (ER−/Her2+) cell lines were performed as above. The fraction of apoptotic cells was significantly higher with M1 vs. ritonavir in the T47D (20 vs. 13%), MDA-MB-231 (40 vs. 20%), and SKBR3 lines (78 vs. 11%).

Example 3

Induction of Reactive Oxygen Species by M1

Induction of Reactive Oxygen Species (ROS), including peroxide and superoxide, were studied in the T47D cell line. Cells were seeded in 6 well plates (~80,000 cells/well) using the appropriate medium, (DMEM with 10% FBS, 1% L-Glu, 1% Sodium Piruvate, and 1% Pen-strep) and exposed to ritonavir (30 μM) and M1 (30 μM) for 24 hours. Subsequently, the medium was removed from the wells and the cells were exposed to DHE (2 μM in PBS) or Carboxy-H2-DCFDA (10 μM in PBS) for 30 minutes. Cells were then trypsinized, washed two times with PBS and analyzed by flow cytometry. Additional cells were exposed to $H_2O_2$ (250 μM) for 2 hours as a positive control for ROS production.

Figure 3:
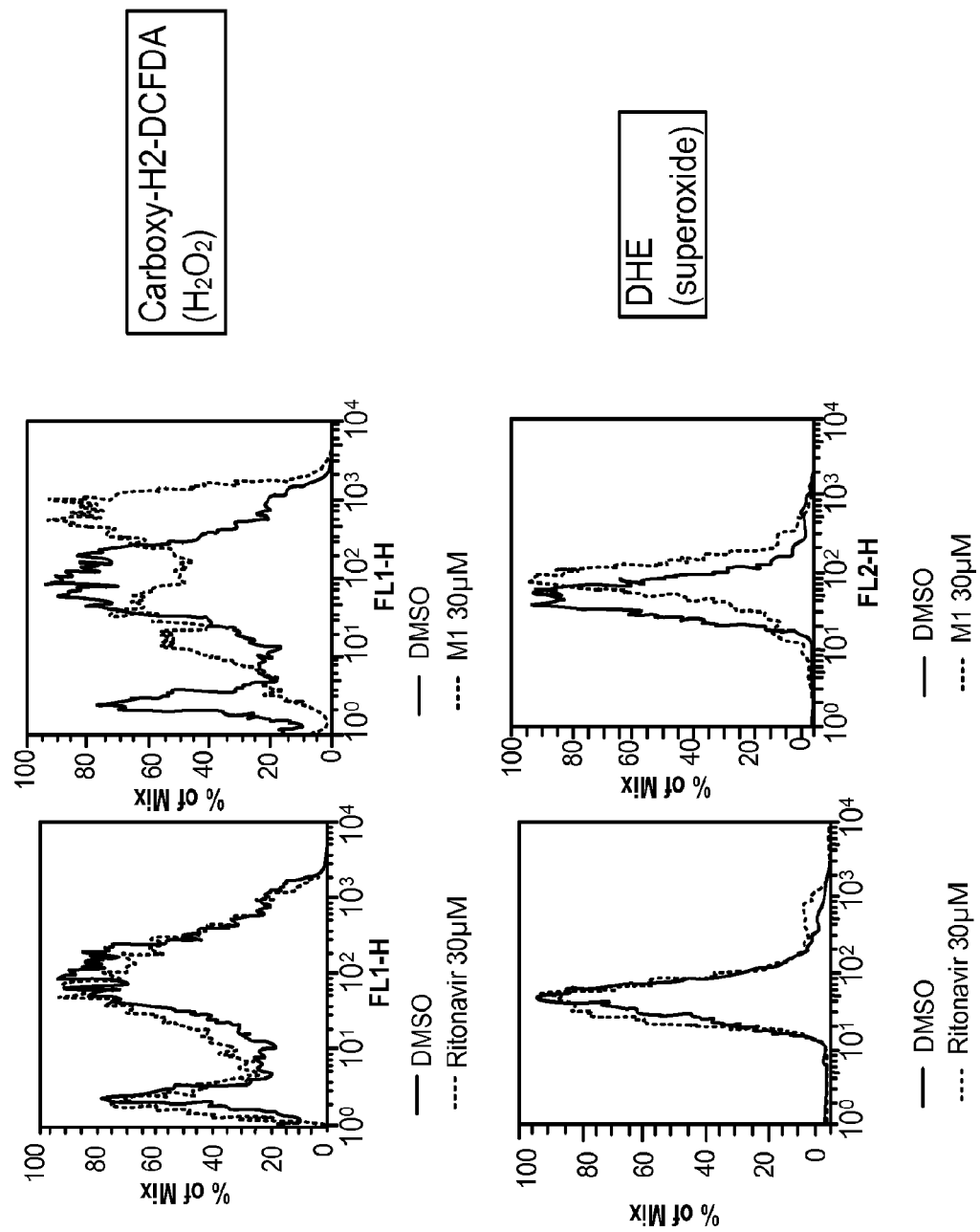
FIG. 3 demonstrates that desthiazolyl ritonavir (M1) induces ROS in the T47D line, while ritonavir does not.

As shown in FIG. 3, M1 induces ROS production in the T47D cell line, while ritonavir does not. A major 70 kDa Hsp90 fragment is observed with M1 treatment, but is 3-fold less abundant with ritonavir (data not shown). This fragment has been previously associated with menadione-induced oxidative stress (see Beck R, Verrax J, Gonze T, et al. Hsp90 cleavage by an oxidative stress leads to its client proteins degradation and cancer cell death. Biochemical pharmacology 2008).

Example 4

Depletion of Hsp90 and Other Proteins by M1

Breast cancer cell lines MDA-MB-231, T47D and SKBR3 were used to study depletion of Hsp90 by M1 and ritonavir. Cells were incubated for 48 hours with 1) ritonavir (R) at its IC$_{50}$ (20 μM for T47D and 40 μM for MDA-MB-231); 2) M1 at ritonavir's IC$_{50}$; or DMSO (control). Cell extracts were made according to the method of Srirangam et al., *Clin Cancer Res.* 2006 Mar. 15; 12(6):1883-96. Briefly, nearly confluent cell monolayers were treated with drug or vehicle (DMSO) for 24 or 48 h. Cells were washed with PBS on ice and scraped in a RIPA buffer containing protease inhibitors including MG-132 and phosphatase inhibitors. The cell lysate protein content was determined by μBCA and equal amounts of protein were loaded per lane. Gel electrophoresis by SDS PAGE was performed with equal protein loading per lane (usually 30 μg) and the separated proteins were transferred to 0.45 μm nitrocellulose filters. The transfer was verified by Ponceau stain of the nitrocellulose filters. The filters were probed by chemiluminescent blotting and then exposed to X-ray film. The signal from the protein of interest was normalized to the GAPDH signal. Student's t-test was used to determine the significance of differences.

Figure 4:
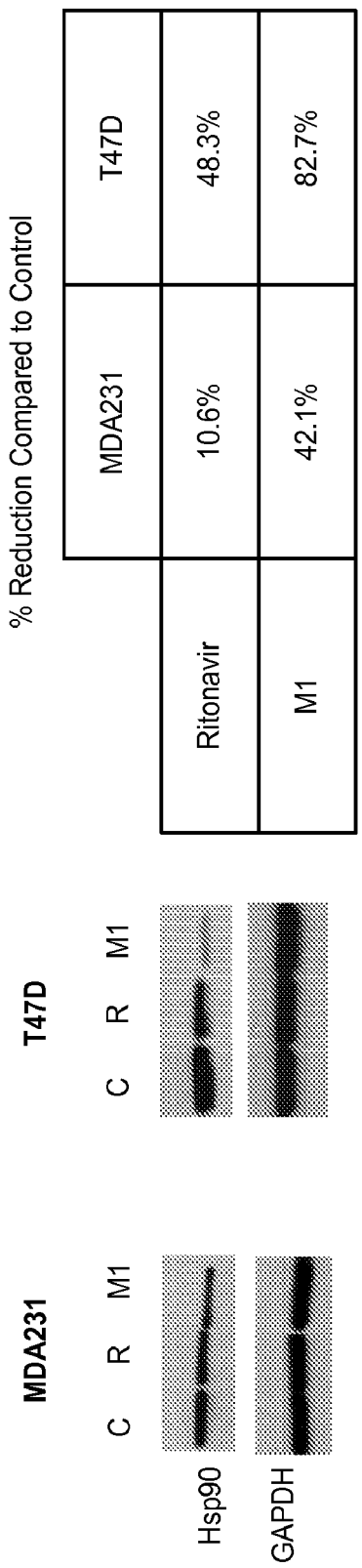
FIG. 4 illustrates desthiazolyl ritonavir (M1) depletion of Hsp90 in the MDA-MB-231 and T47D breast cancer lines.

M1 was more potent than ritonavir in reducing Hsp90 levels in the T47D and MDA-MB-231 lines (FIG. 4; Table 1), while neither drug reduced Hsp90 in the SKBR3 line. M1 was also more potent in reducing total Akt, phospho-Akt, GSK3beta, c-src, and survivin for all three breast cancer lines (P<0.05 by Student's t test). Both M1 and ritonavir reduced the G1/S regulatory protein Cyclin D1 in MDA-MB-231 and T47D cell lines (P<0.05 by Student's t test), but only M1 reduced the G1/S regulator protein in the SKBR3 cell line. For the ER+ T47D line, M1 was more potent in reducing ER alpha (P<0.05 by Student's t test). Importantly, M1, but not ritonavir, reduced the expression of surface HER2 in the SKBR3 line, up to 80% (P<0.05 by Student's t test).

Example 5

Inhibition of a Murine Breast Cancer Xenograft

Six-8 weeks old female nude mice (nu$^-$/nu$^-$) (Charles River Laboratories International, Inc., MA) were injected into a right mammary fat pad with $1 \times 10^6$ log-phase MDA-MB-231. Mice were monitored bi-weekly for weight and tumor growth. When tumors reached a volume of approximately 30-40 mm$^3$ (calculated according to the formula: volume (mm$^3$)=(length)(width)$^2$/2), mice were randomized into three groups (each group n=10). One group of mice was injected daily i.p. with ritonavir (20 mg/Kg in 100 μl of ethanol-Tween 80), the second with M1 (20 mg/Kg in 100 μl of ethanol-Tween 80), and the third with vehicle only (100 μl of ethanol-Tween 80). The dose of drugs used in this experiment (20 mg/Kg) is the maximum tolerated dose exhibited by nude mice for M1. Mice were weighted and their tumors were measured twice a week for the entire duration of the treatment (42 days).

One hour after the last drug/vehicle injection plasma, tumors, lungs, liver, tongue, and skin were collected from each mouse. Plasma was stored at −80° C.; half of the tissues were treated to prepare paraffin blocks, and half were frozen in liquid nitrogen and stored at −80° C.

Figure 5C:
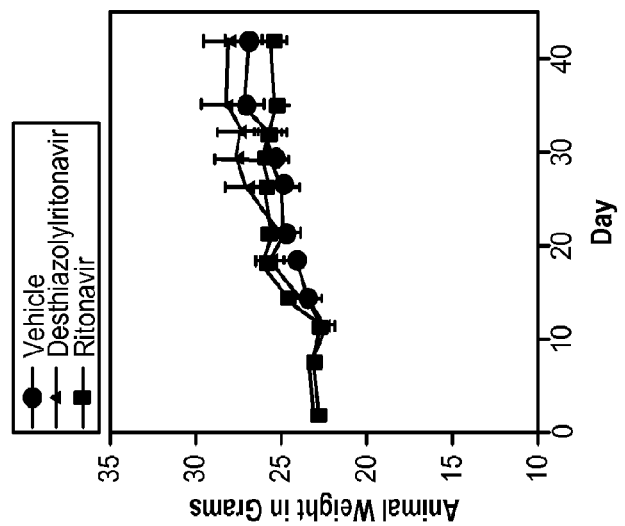
FIG. 5 shows that desthiazolyl ritonavir inhibits a murine breast cancer xenograft and is more potent than ritonavir.
Figure 5B:
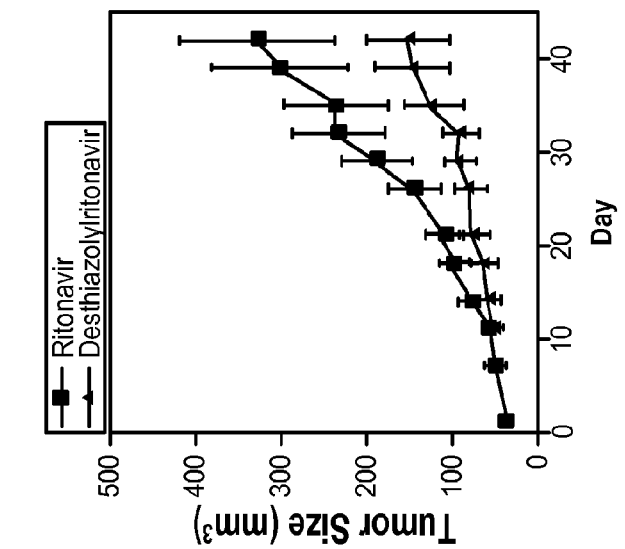
Figure 5A:
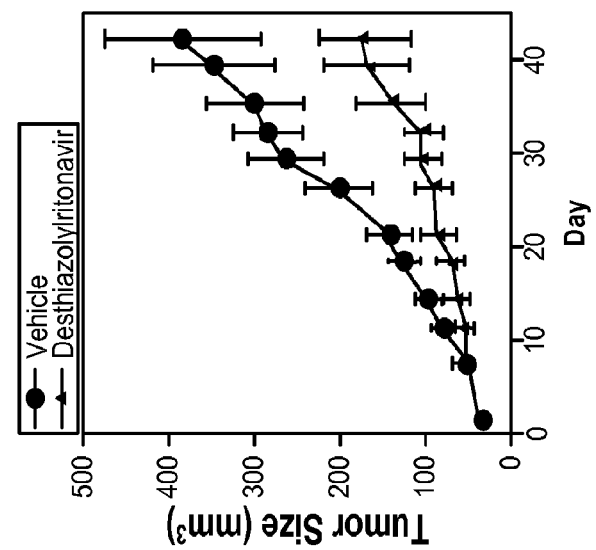

As shown in FIG. 5A, M1 exhibited statistically significant (by the Student t test) delayed tumor growth compared to mice treated with only the vehicle. Also, when the results obtained with M1 are compared to that from ritonavir (see FIG. 5B), M1 again exhibited a statistically significant delay in tumor growth. Although ritonavir inhibits an MDA-MB-231 xenograft at its MTD (40 mg/Kg), it is ineffective at half its MTD (20 mg/Kg). In contrast, M1 tested at its MTD (20 mg/Kg) reduced the average tumor size 2-fold at 42 days of follow-up (P<0.05 by Student's t-test) (FIG. 5A,B). Animal weight loss did not occur with either drug (FIG. 5C).

Example 6

M1 Inhibits Breast Cancer Cell Proliferation

Figure 6:
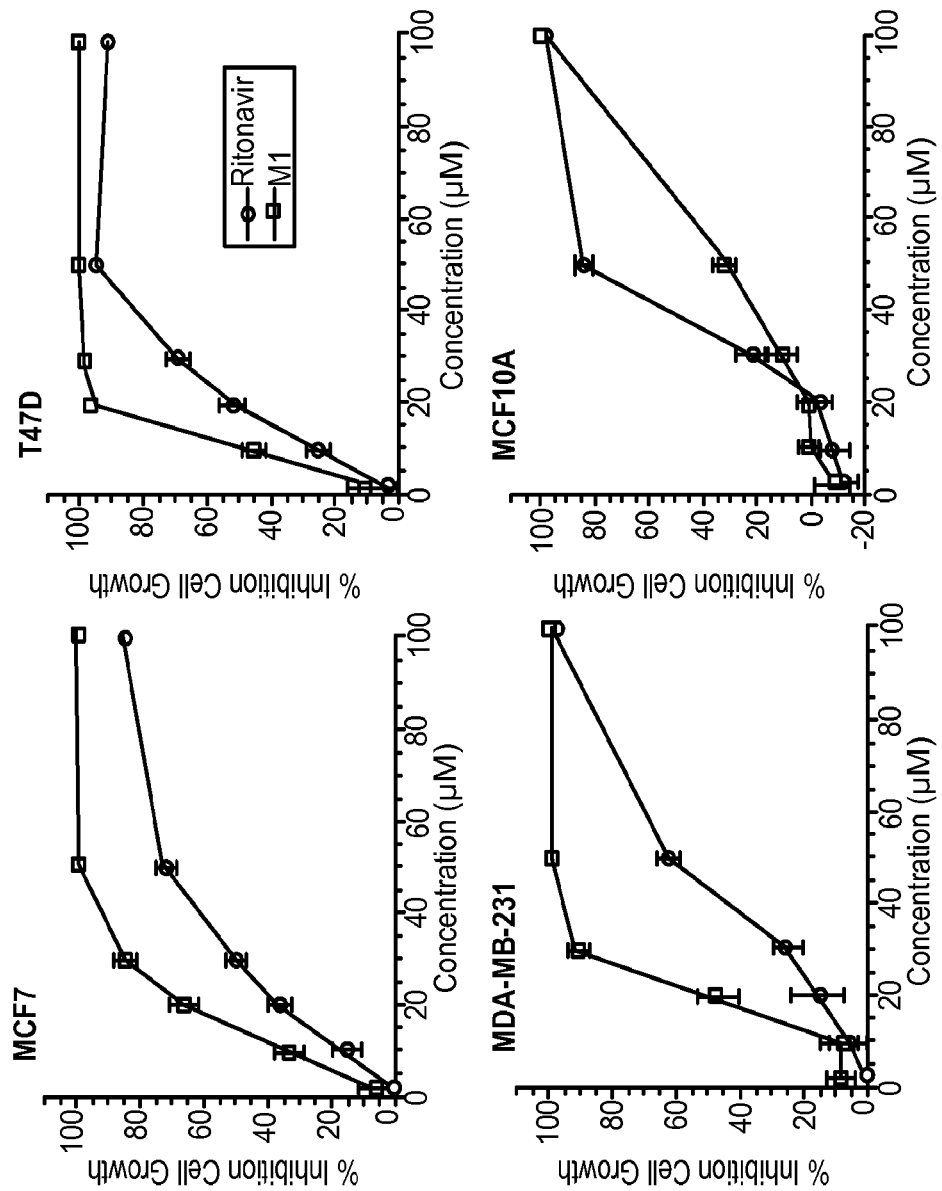
FIG. 6 demonstrates that desthiazolyl ritonavir is a more potent inhibitor of breast cancer cell lines than ritonavir, but is a less potent inhibitor of a non-transformed line.

M1 inhibition of proliferation of MCF7 (ER+), T47D (ER+), MDA-MB-231 (triple negative), SKBR3 (ER−/Her2+), and the non-transformed mammary line MCF10A were studied. Cells (n=2000/well) were seeded in 96 well plates with drug or vehicle (DMSO) on D1 and after 48 h the cell number was determined by MTT assay. In all the breast cancer lines tested, M1 exhibited a lower IC$_{50}$ compared to ritonavir: 10, 15, 22, and 12 μM observed with M1 vs. 23, 28, 40, and 33 µM observed with ritonavir for the T47D, MCF7, MDA-MB-231, and SKBR3 lines, respectively (FIG. 6; SKBR3 not shown). In contrast, M1 exhibited a higher $IC_{50}$ for the non-transformed breast epithelial line MCF10A: 45 vs. 31 µM for ritonavir (FIG. 6).

Example 7

M1 as an Anti-HER2 Agent

SKBR3 cells were plated at a density of 80,000 cells/well in 6-well plates. After 18 hours, cells were exposed to ritonavir (33 µM), Desthiazolyl Ritonavir (M1) (33 µM), or DMSO. After 24 hours, cells were trypsinized, spun down, and resuspended in 50 µL of Staining Buffer (PBS 1% BSA). Cells were then incubated with anti-HER2 Ab FITC (Chemicon International; MAB4083F) for 30 minutes (on-ice and in the dark). Control cells were incubated with mouse IgG1 FITC (Biolytex). Cells were washed two times with Washing Buffer (PBS 0.1% Tween-20), resuspended in 100 µL of PBS, and acquired using FACSCalibur flow cytometer.

Figure 7:
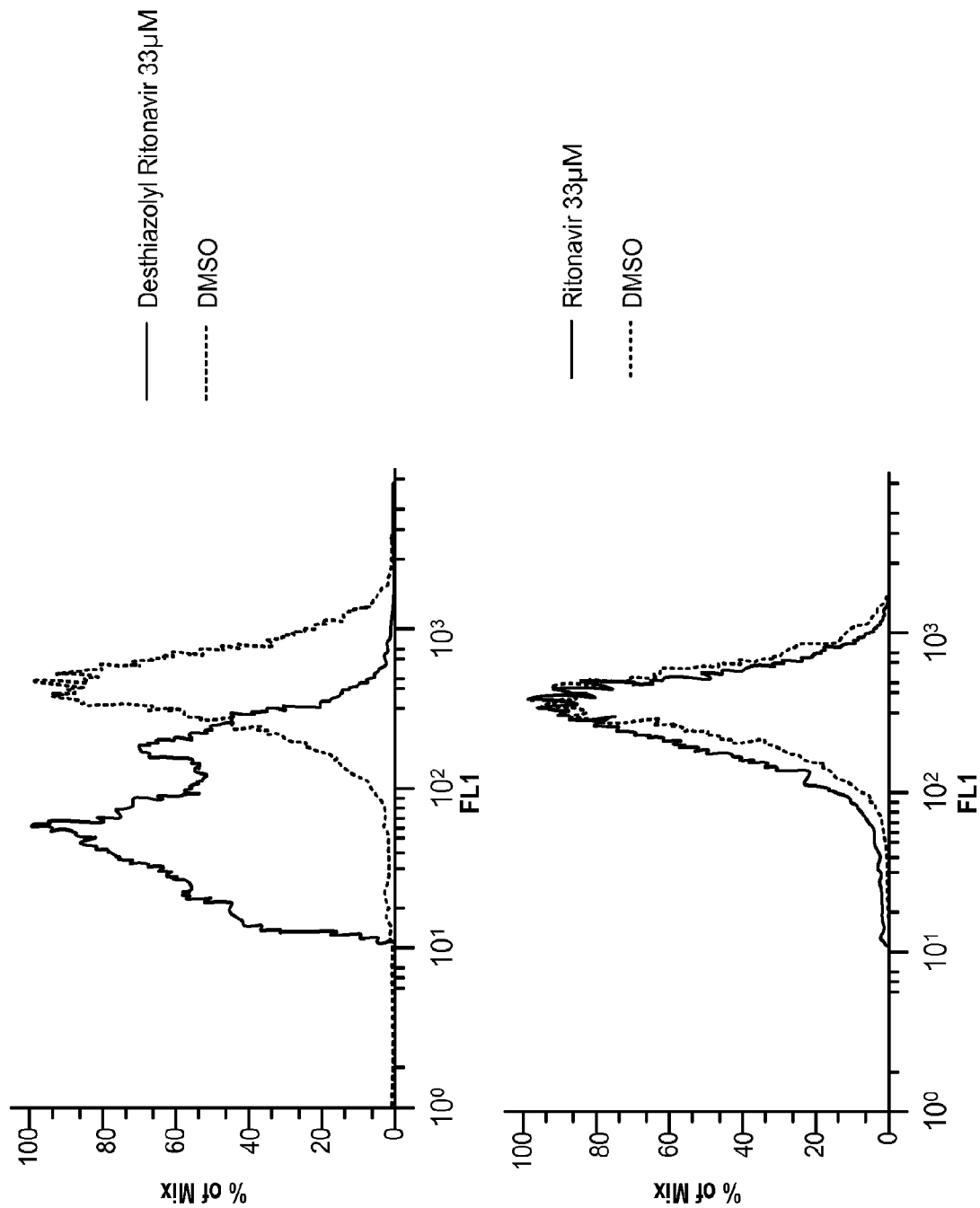
FIG. 7 illustrates M-1 activity an anti-HER2 agent.

As demonstrated in FIG. 7, M1 exhibited anti-HER2 functionality, while ritonavir did not.

Example 8

Synergy of M1 and Ritonavir

Cells were plated in 96 well plates, after overnight incubation, ritonavir and M-1 in specific ratios or DMSO vehicle were added to the cells and incubated for 48 hours or longer. Then MTT (thiazole blue tetrazolium bromide) was added (0.5 mg/ml) and incubated for 2 hours followed by centrifugation in an Allegra plate centrifuge at 2000 rpm for 5 minutes. Cell pellets were dissolved in DMSO. Absorbance at 540 nm was determined in a colorimetric plate reader. The isobologram method of Chou and Talalay was utilized in which the ratio of M-1 and ritonavir was fixed according to the ratio of the IC50's and then tested across a several log range above and below the $IC_{50}$ of M-1. See *Adv Enzyme Regul*. 1984; 22:27-55. The Calcusyn program calculates the Chou/Talalay combination index.

Figure 8:
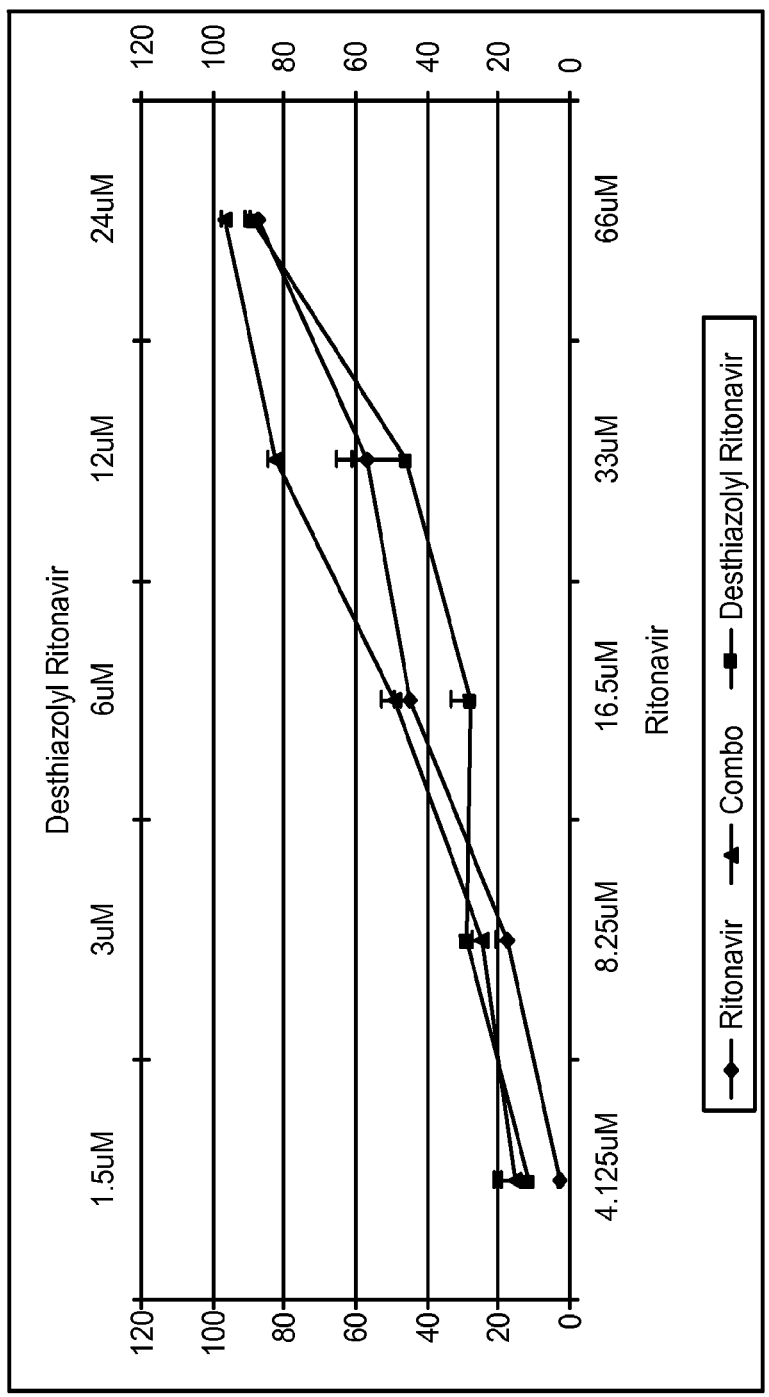
FIG. 8 shows the effects of a 2.75:1 combination of M1:ritonavir in the SKBR3 cell line.
Figure 9:
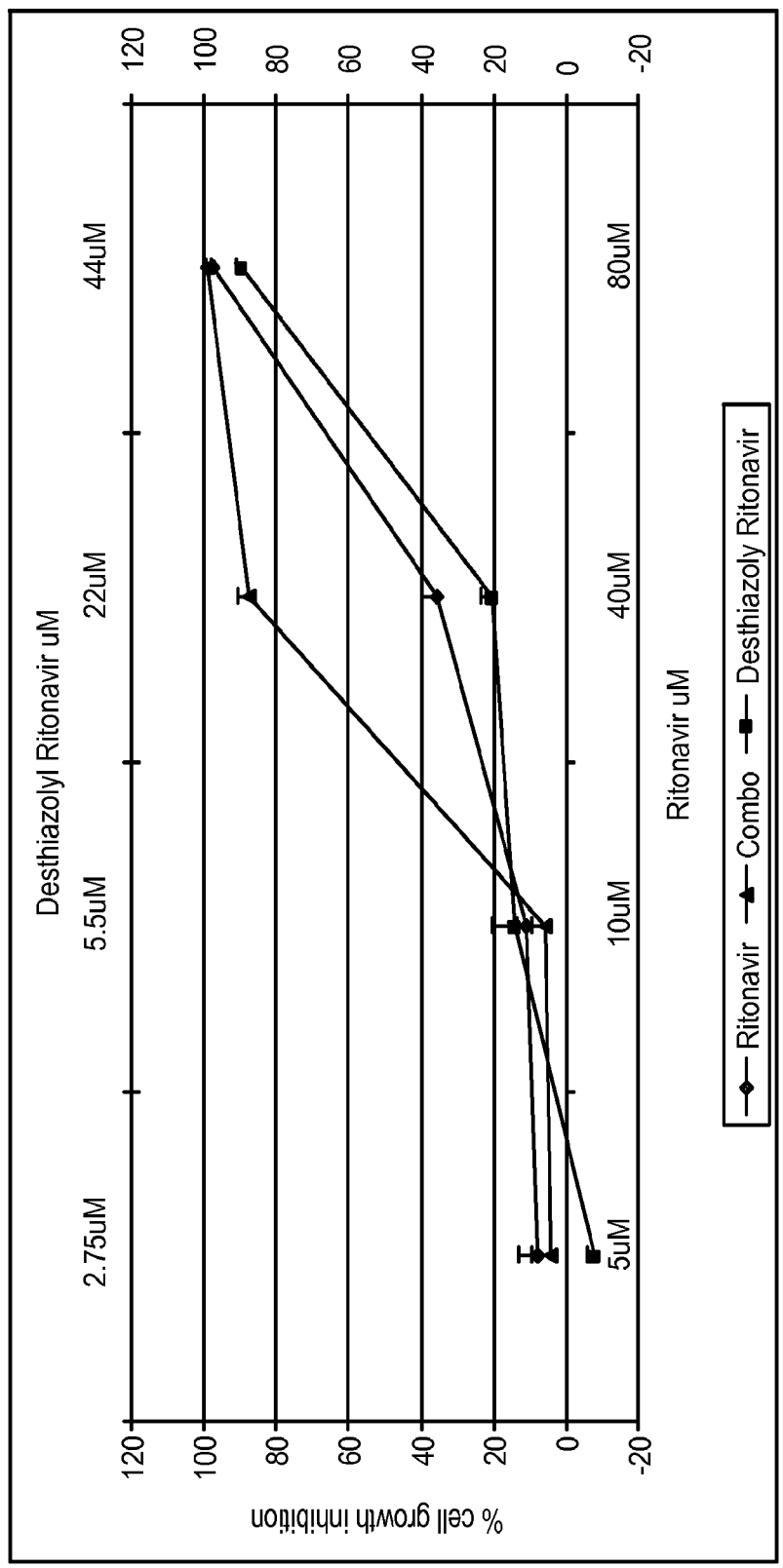
FIG. 9 shows the effects of a 1.81:1 combination of M1:ritonavir in the MDA-MB-231 cell line.
Figure 10:
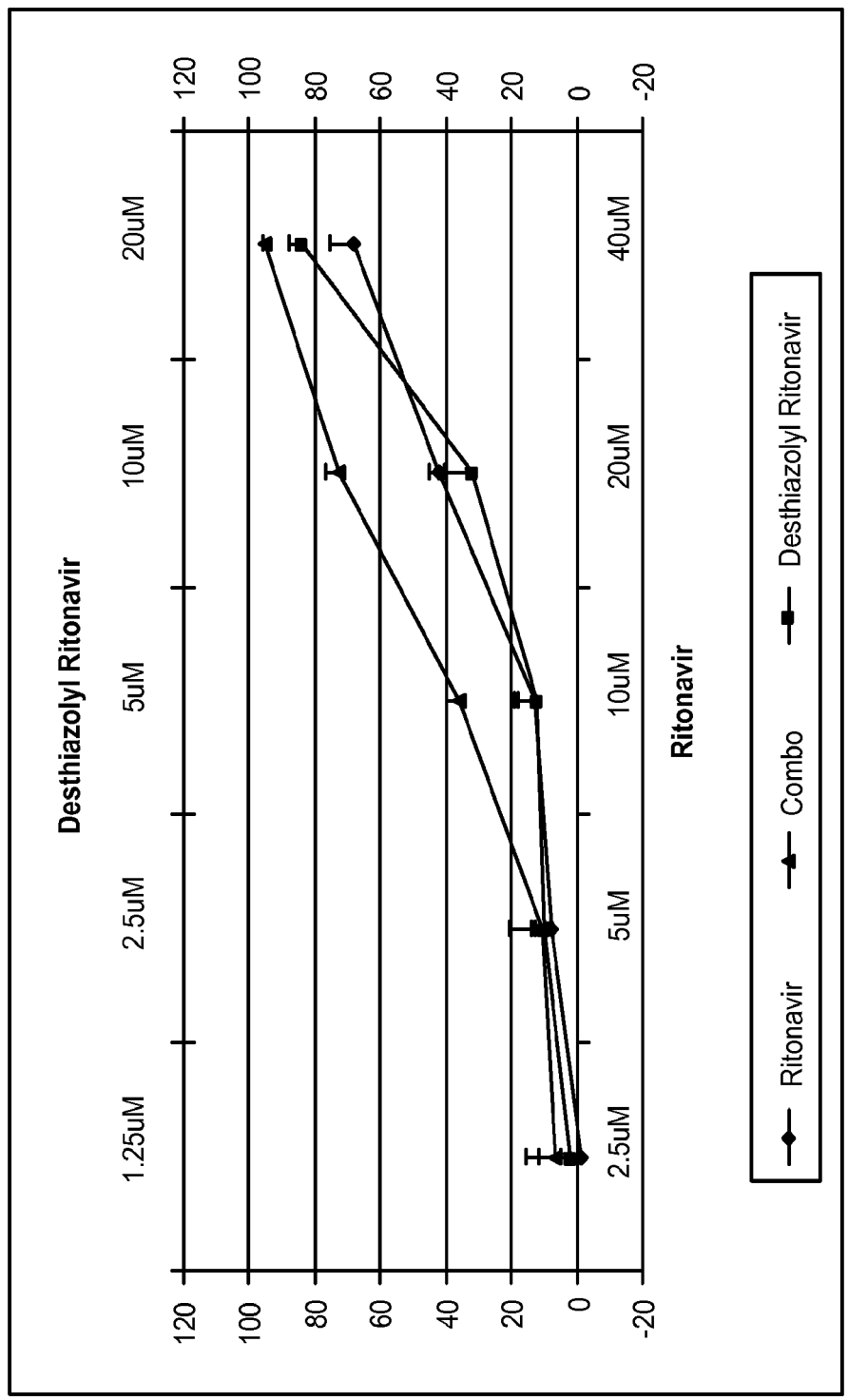
FIG. 10 shows the effects of a 2:1 combination of M1:ritonavir in the T47D cell line.

A CI value less than 1 is indicative of a synergistic effect (Chou & Talalay's algorithm). Results indicated that the M1/ritonavir combination has a synergistic effect at the ratios tested (see FIGS. 8-10 and Tables 5-7).

TABLE 5

CI values for a 2.75:1 combination of M1:ritonavir in SKBR3

|    | ED50    | ED75    | ED90    |
|----|---------|---------|---------|
| CI | 1.17021 | 1.04652 | 0.95200 |

TABLE 6

CI values for a 1.81:1 combination of M1:ritonavir in MDA231

|    | ED50    | ED75    | ED90    |
|----|---------|---------|---------|
| CI | 1.26393 | 1.05903 | 0.88736 |

TABLE 7

CI values for a 2:1 combination of M1:ritonavir in T47D

|    | ED50    | ED75    | ED90    |
|----|---------|---------|---------|
| CI | 1.09543 | 1.15607 | 1.26300 |

Example 9

Association Between Hsp90 and M1

Purified mammalian Hsp90 was attached to a CM-5 BIAcore chip through an NHS ester linkage. After attachment of the Hsp90 and blocking the chip with BSA, M1 drug or a 17-AAG control was circulated through a microfluidic circuit and change in refractive index was measured by quantification of the RU value for each drug concentration. In the case of the 17-AAG control the binding was saturable and based on the $k_{on}$ and $k_{off}$ measurements, the KD was estimated to be in the 1 microM range. In contrast, although M-1 binds, the binding is not saturable, as indicated by the rising RU value with increasing M-1 concentration. This means that there are significant differences in the binding of M-1 and may indicate alteration of the Hsp90 structure.

Figure 11:
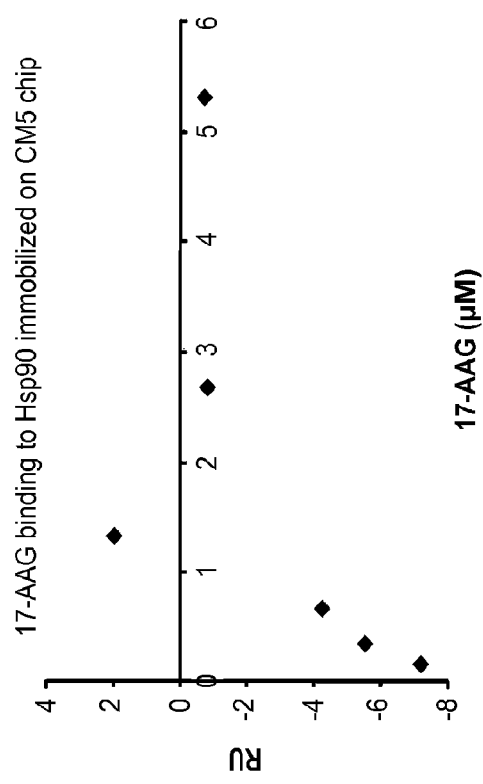
FIG. 11 demonstrates M1 binding to Hsp90 on a CM5 chip.
Figure 11:
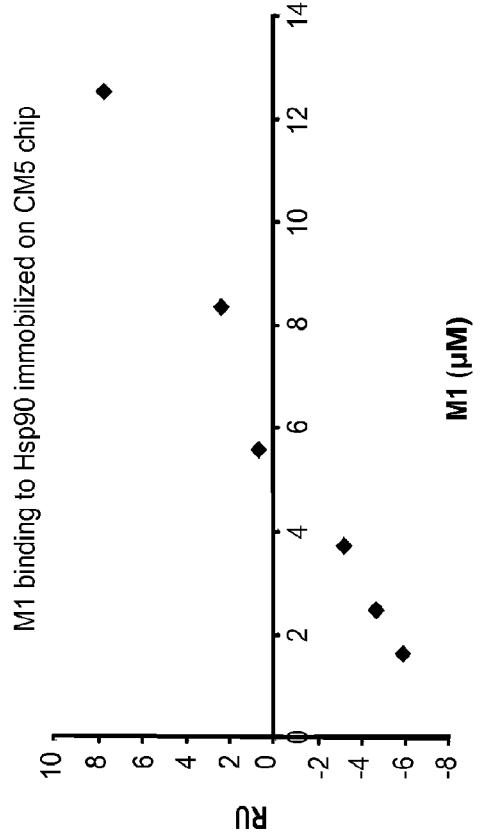

FIG. 11 indicates the presence of an association between M1 and Hsp90.

Example 10

Effect of siRNA on Proliferation of Breast Cancer Lines

Figure 12A:
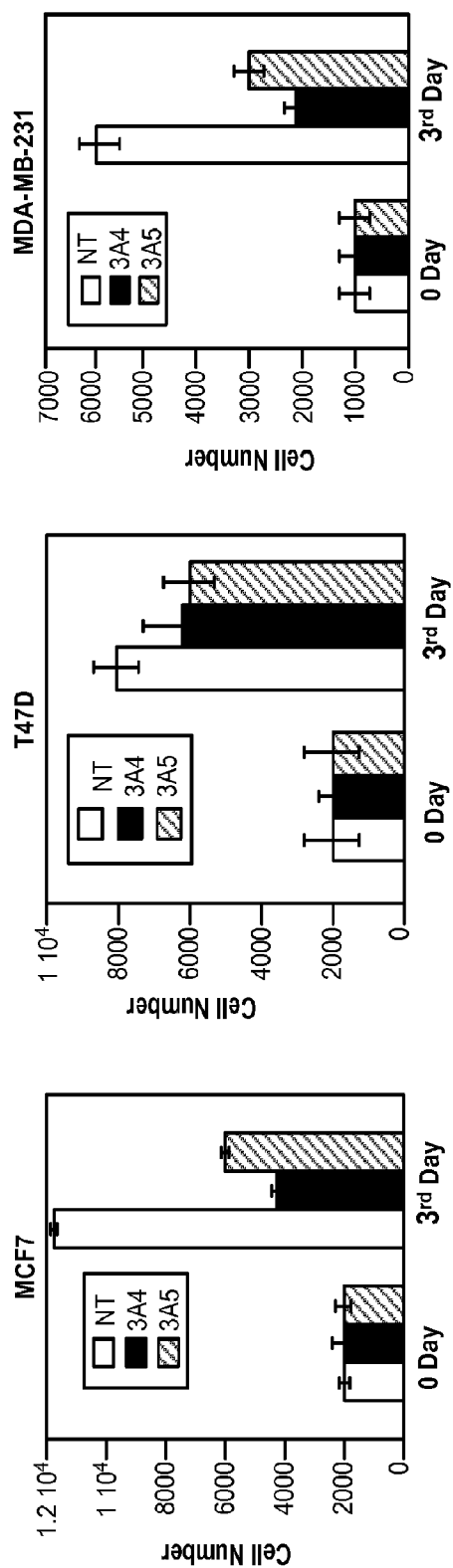
FIG. 12 shows the effect of siRNA on proliferation of breast cancer lines.
Figure 12B:
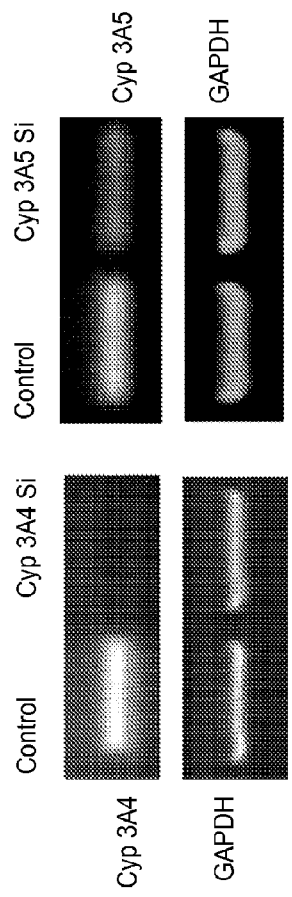

A pool of four siRNA (see Table 8) was used to inhibit the CYP3A4/5 expression in the MCF-7, T47D and MDA-MD-231 breast cancer cell lines using transient transformation. The three breast cancer lines were transiently transfected with non-target (Control), CYP3A4 and CYP3A5 siRNA. Proliferation of the lines was monitored using MTT assay (see FIG. 12A). The P value is less than 0.05 as compared to the non-target control. FIG. 12B shows the semiquantitative RT-PCR indicated comparative inhibition by siRNA in the MCF7 line. The RT-PCR analysis shows that a 90% reduction is observed in the case of CYP3A4 and a 60% reduction is observed in the case of CYP3A5. The Samples were normalized with GAPDH and done in triplicates.

TABLE 8 siRNA sequences used for targeting specific gene sequences

| Species No. | Name | | Sequence | SEQ ID NO. | Molecular Weight |
|---|---|---|---|---|---|
| 1 | siCONTROL (Non-Targeting) | I- | AUGAACGUGAAUUGCUCAA | 1 | 13358 |
|   |   | II- | UAAGGCUAUGAAGAGAUAC | 2 | 13358 |
|   |   | III- | AUGUAUUGGCCUGUAUUAG | 3 | 13358 |
|   |   | IV- | UAGCGACUAAACACAUCAA | 4 | 13358 |

TABLE 8-continued siRNA sequences used for targeting specific gene sequences

| Species No. | Name | | Sequence | SEQ ID NO. | Molecular Weight |
|---|---|---|---|---|---|
| 2 | siCYP3A4 (Targeting CYP3A4 | I-<br>II-<br>III-<br>IV- | GAAAGAAAGUCGCCUCGAA<br>GGAGGAAAUUGAUGCAGUU<br>CAUCCCAAUUCUUGAAGUA<br>CCAAGAGAAGUUACAAAUU | 5<br>6<br>7<br>8 | 13388<br>13373<br>13358<br>13343 |
| 3 | siCYP3A5 (Targeting CYP3A5) | I-<br>II-<br>III-<br>IV- | GCACUAAGAAGUUCCUAAA<br>GAAAUUAGACACGCAAGGA<br>GAAGAAGGACAGCAUAGAU<br>UGACACAGAGUGCUAUAAA | 9<br>10<br>11<br>12 | 13358<br>13373<br>13373<br>13358 |

Example 11

Effect of CYP3A inhibitor Azamulin on the Proliferation of Breast cancer Lines

Figure 13:
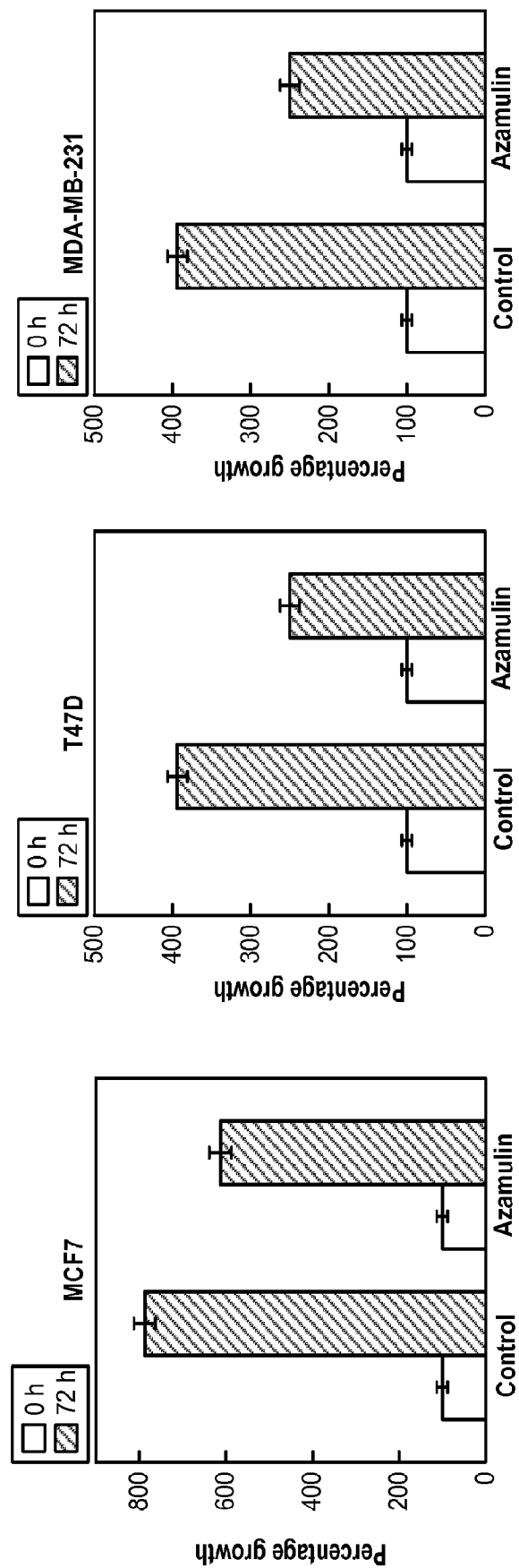
FIG. 13 illustrates the effect of the CYP3A inhibitor Azamulin on the proliferation of breast cancer lines.

The effect of Azamulin was tested in the three breast cancer lines MCF7, T47D and MDA-MB-231. A concentration of 5 µM Azamulin was used in this study. This concentration corresponds to the $IC_{50}$ of CYP3A inhibition for this drug. The cells were plated in a phenol red free charcoal stripped serum compensated media. Cell proliferation was determined after 72 hrs. See FIG. 13.

Example 12

CYP3A4 inhibition by siRNA results in decreased migration of MDA-MB-231 Cells

Figure 14:
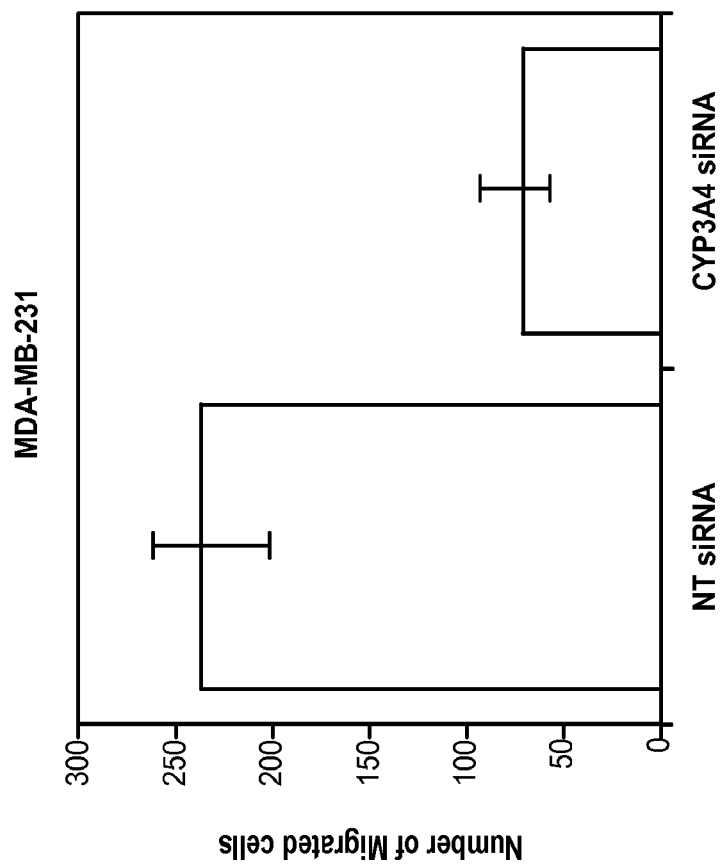
FIG. 14 shows CYP3A4 inhibition by siRNA results in decreased migration of MDA-MB-231 cells.

The effect of CYP3A4 inhibition on migration was tested using the MDA-MB-231 breast cancer cell line in a Boyden chamber assay. The cells were transfected with a non-target (NT) and CYP3A4 siRNA and the migration efficiency on the $4^{th}$ day was determined. Cells were plated on the upper chamber ($1.5 \times 10^5$) and porous filter (8 µM) was used to separate the two chambers. Cells were incubated for 4 hours, migrated cells were fixed, stained with eosin and methylene blue, and counted. Both the NT and the siRNA is a pool of four different sequences. See FIG. 14.

Example 13

CYP3A4 shRNA MCF7 Clones Show Reduced Migration

Figure 15:
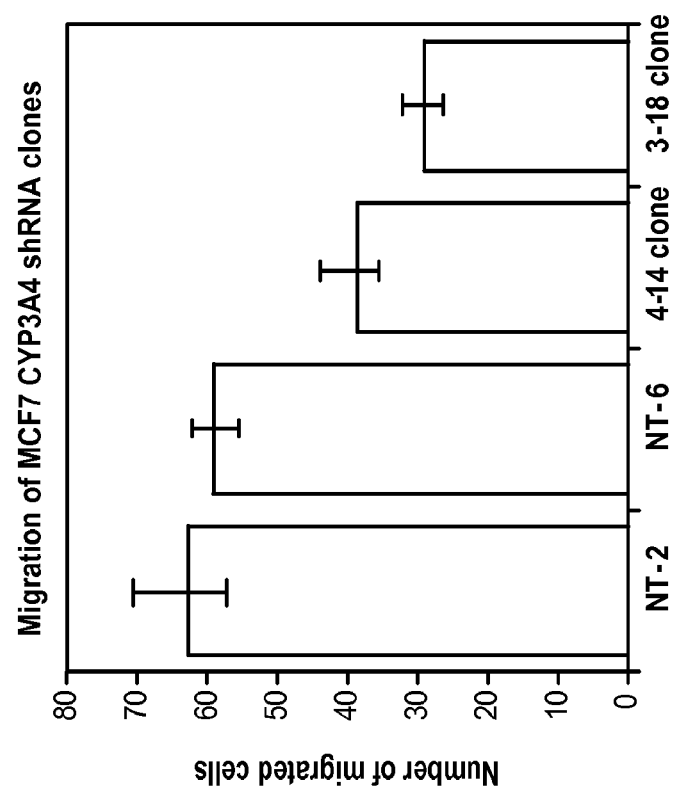
FIG. 15 demonstrates that CYP3A4 shRNA MCF7 clones show reduced migration.

The migration efficiency of the MCF7 shRNA clones were tested in a Boyden chamber assay and compared to shRNA containing non-target sequences (NT). Cells were plated in the upper chamber ($1.5 \times 10^5$) and incubated for 6 hours using a 5% serum as a chemoattractant. The cells were treated as described in Example 12 and counted. The CYP3A4 shRNA sequences were designed based on two separate target sequences. See FIG. 15.

Example 14

CYP3A4 Inhibits Anchorage Independent Growth

Figure 16:
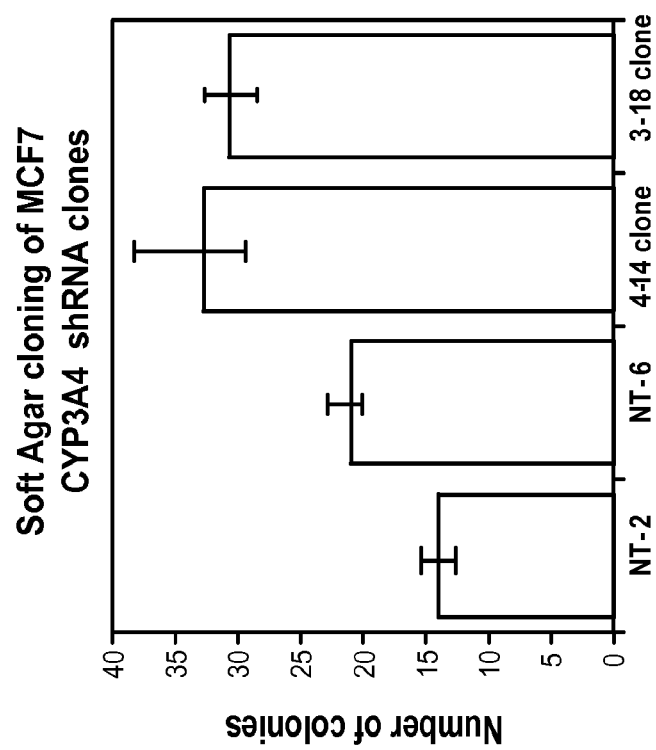
FIG. 16 illustrates that CYP3A4 inhibits anchorage independent growth.

CYP shRNA (4-14 and 3-18) and NT clones (NT-2 and NT-6) were plated (10,000 cells/6 well) with soft agar containing 10% serum media on a hard agar base. The cells were incubated for 7-10 days and counted in reference to a 10×10 grid. Five representative areas were counted from each set, and each set was performed in triplicates. The CYP shRNA clones exhibited increased colonies as compared to NT clones. See Table 9 and FIG. 16.

TABLE 9

Relative expression of the CYP3A4 mRNA in the shRNA clones by q-PCR

| | Relative # (% of control) |
|---|---|
| NT-2 | 100 ± 11 |
| NT-6 | 88 ± 14 |
| 4-14 | 42 ± 4 |
| 3-18 | 69 ± 6 |

Example 15

CYP3A4 Regulates Breast Cancer Cell Motility

Figure 17:
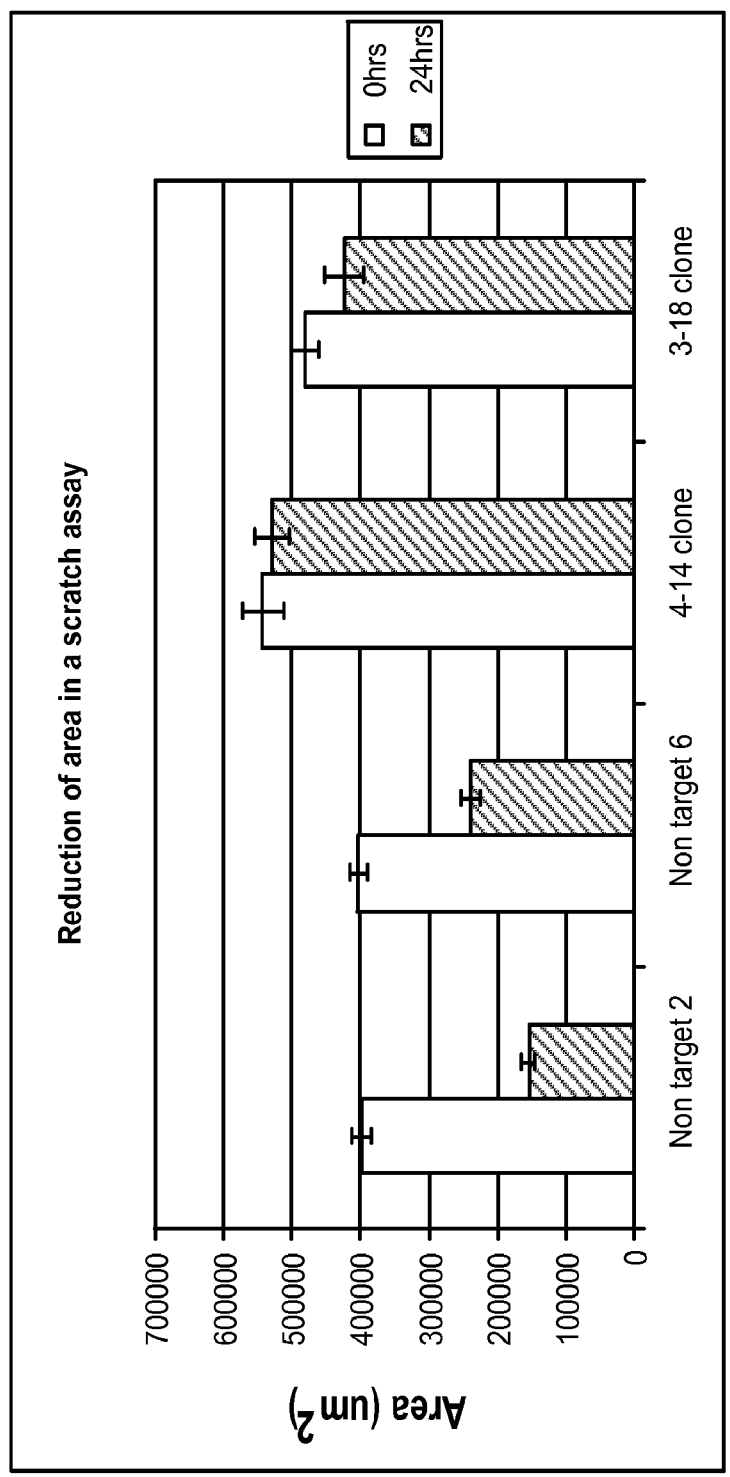
FIG. 17 shows the results of a scratch test migration assay.

A standard scratch test assay was used to determine the effect of CYP3A4 on the motility of breast cancer cells. Cells were plated in 6-well plates and grown to confluence. The cells were then scratched using a pipette tip, and the scratched area was measured using Leica application software. After 24 hours the area was measured again. The assay is performed in triplicate (three wells per condition) and an average of 5 pictures per well were taken per time point. CYP shRNA (4-14 and 3-18) and NT clones (NT-2 and NT-6) were studied. See FIG. 17.

Examples 10-15 above illustrate the effect of CYP3A4 regulation and inhibition on the proliferation, adhesion, and motility of various breast cancer cell lines.

Example 16

The Adenocarcinoma Non-Small Cell Lung Cancer Line H522 Exhibits Greater Sensitivity to M1

H522 adenocarcinoma non-small cell lung cancer cell proliferation was measured in 96-well plates by a 3-(4,5-dimethylthiazol-2-yl)-2,5 diphenyltetrazolium bromide (MTT) assay that measures reduction of MTT in 96-well plates (see Ohno M, Abe T. *J Immunol Methods,* 1991 Dec. 15; 145(1-2):199-203). The cells were exposed to 10 to 80 µmol/L ritonavir, M1 or DMSO vehicle for 48 hours and proliferation was subsequently quantified by MTT assay. The MTT was added to the medium at the endpoint and the plate was incubated for 2 hours. The plate was then centrifuged in an Allegra plate centrifuge at 2000 rpm for 5 minutes. The medium was removed, and the pellet was dissolved in 100 μL of DMSO per well. The pellet was dissolved using a gently vibrating platform. The plates were read with a BioTek Synergy plate reader in colorimetric mode at 540 nm. Each assay was performed in octuplicate for each data point.

Figure 18:
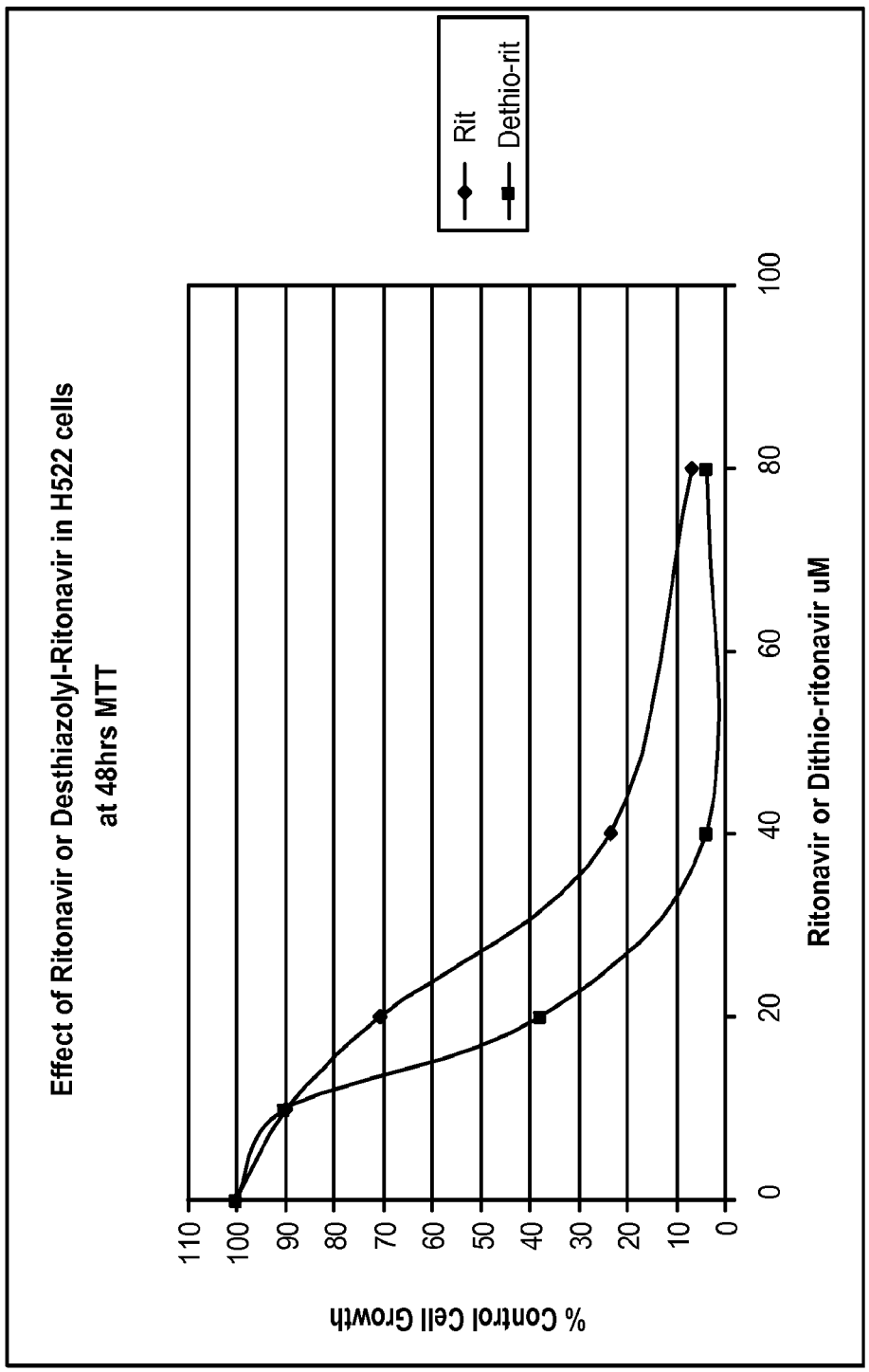
FIG. 18 illustrates the sensitivity of the adenocarcinoma non-small cell lung cancer line H522 to M1

As shown in FIG. 18, measured cell proliferation was lower in cells exposed to M1 compared to cells exposed to ritonavir or DMSO.

Example 17

Reduction of ER+ by M1

Figure 19:
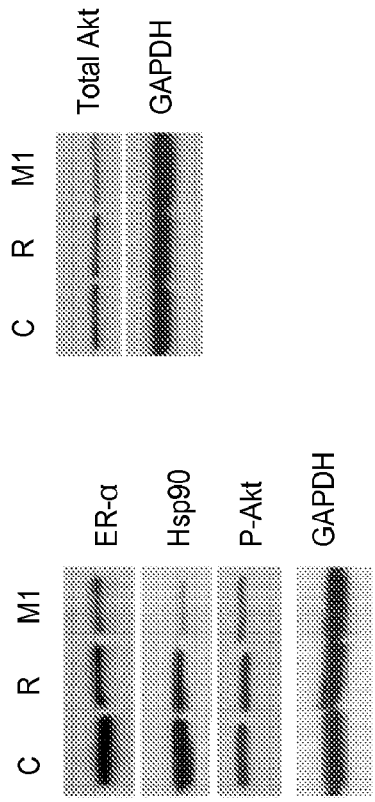
FIG. 19 demonstrates reduction of ER+ by M1.
Figure 19:
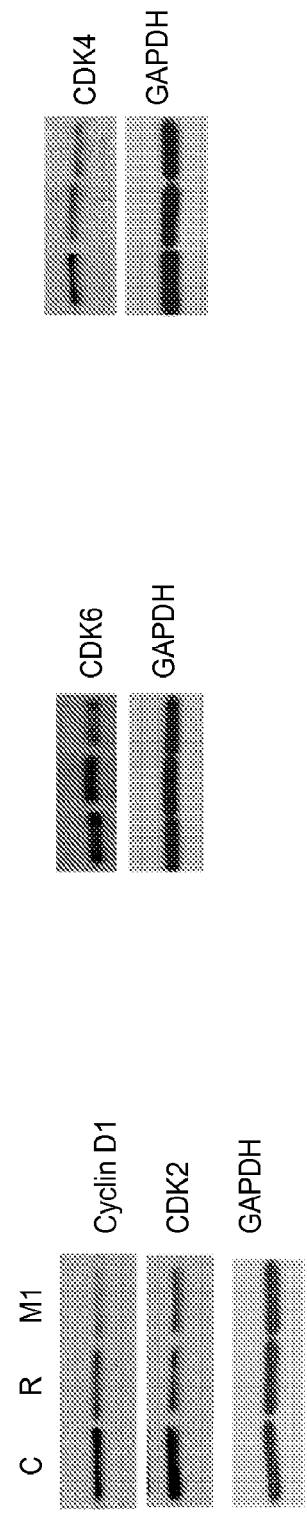

An ER+ line, T47D, was treated with M1 or ritonavir for 24 or 48 hours. The cells were grown to confluence and treated with drug or DMSO vehicle. The cells were scraped on ice into RIPA buffer containing protease inhibitors including MG-132 and phosphatase inhibitors as published (see Srirangam et al. *Clincal Ca Research* 2006). The RIPA lysate was subjected to electrophoresis, blotted and probed with the appropriate antibodies. Densitometry was performed and quantified as shown in Table 10 and FIG. 19.

TABLE 10

| T47D | % Reduction Ritonavir | P | % Reduction M1 | P |
| --- | --- | --- | --- | --- |
| Total Akt | 5.04 | 0.698 | 56.57 | 0.007 |
| Phospho Akt | 9.98 | 0.318 | 56.36 | 0.006 |
| ER-α | 33.24 | 0.04 | 56.41 | 0.007 |
| Hsp90 | 48.3 | 0.031 | 82.70 | 0.0004 |
| Cyclin D1 | 42.87 | 0.022 | 45.64 | 0.029 |
| CDK2 | 49.91 | 0.016 | 51.02 | 0.014 |
| CDK4 | 23.99 | 0.09 | 2.23 | 0.83 |
| CDK6 | 11.64 | 0.25 | 21.05 | 0.051 |

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating cancer in a subject, the method comprising administering to the subject a therapeutically effective amount of a compound of formula I:

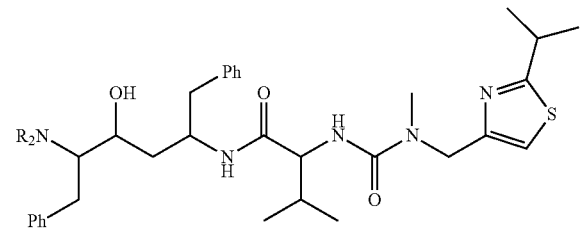

wherein each R is independently H or $C_{1-6}$ alkyl, or a pharmaceutically acceptable salt form thereof.

2. The method of claim 1, wherein the compound of formula I is:

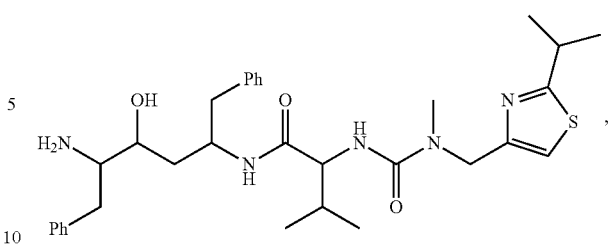

or a pharmaceutically acceptable salt form thereof.

3. The method of claim 1, wherein the subject is a human.

4. The method of claim 1, wherein the cancer is selected from:
bladder cancer, brain cancer, breast cancer, colorectal cancer, cervical cancer, gastrointestinal cancer, genitourinary cancer, head and neck cancer, hematologic cancer, lung cancer, ovarian cancer, prostate cancer, renal cancer, skin cancer, and testicular cancer.

5. The method of claim 4, wherein the cancer is breast cancer.

6. The method of claim 5, wherein the breast cancer is ER+ breast cancer.

7. The method of claim 5, wherein the breast cancer is her2− or her2+ breast cancer.

8. The method of claim 5, wherein the breast cancer is triple negative breast cancer.

9. The method of claim 1, wherein the subject is postmenopausal.

10. The method of claim 1, wherein the subject has a cancer associated with resistance to a known anticancer drug regime.

11. The method of claim 10, wherein the anticancer drug regime is selected from one or more of Taxol, Herceptin, Avastin, 5-fluouracil and epirubicin.

12. The method of claim 10, wherein the cancer comprises cells that express a P glycoprotein (MDR), a multidrug resistance-associated protein (MRP), or a breast cancer resistance protein (BCRP).

13. A pharmaceutical composition comprising a compound of formula I:

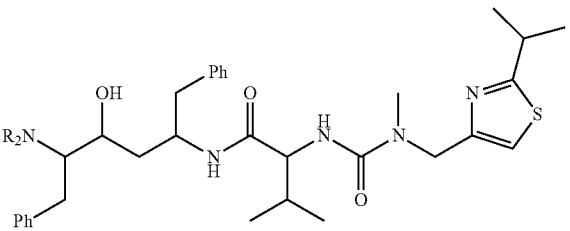

wherein each R is independently H or $C_{1-6}$ alkyl, or a pharmaceutically acceptable salt form thereof.

14. The composition of claim 13, wherein the composition further comprises a carrier, excipient, or diluent.

15. The composition of claim 13, wherein the composition further comprises a pain relief agent, an antinausea agent, ritonavir, or an additional anticancer agent.

16. The method of claim 4, wherein the hematologic cancer is acute myeloid leukemia.

* * * * *

UNITED STATES PATENT AND TRADEMARK OFFICE
CERTIFICATE OF CORRECTION

PATENT NO.         : 8,501,792 B2                                       Page 1 of 1
APPLICATION NO.    : 12/867845
DATED              : August 6, 2013
INVENTOR(S)        : David A. Potter It is certified that error appears in the above-identified patent and that said Letters Patent is hereby corrected as shown below:

In the Specification

Column 1, Lines 18-21, please delete "Certain aspects of the disclosure provided herein were supported by Grant No. R01-CA113570, granted by the National Institutes of Health. The Government has certain rights in the invention." and insert -- This invention was made with government support under R01-CA113570 awarded by the National Institutes of Health. The government has certain rights in the invention. --, therefor.

In the Claims

Column 27, Line 53 (Claim 1), after the compound structure, please insert -- I --, therefor.

Column 28, Line 34 (Claim 11), please delete "5-fluouracil" and insert -- 5-fluorouracil --, therefor.

Column 28, Line 36 (Claim 12), please delete "P glycoprotein" and insert -- P-glycoprotein --, therefor.

Column 28, Line 45 (Claim 13), after the compound structure, please insert -- I --, therefor.

Signed and Sealed this
Eighth Day of April, 2014

Michelle K. Lee
*Deputy Director of the United States Patent and Trademark Office*